US008357637B2

(12) United States Patent
Glimcher et al.

(10) Patent No.: US 8,357,637 B2
(45) Date of Patent: Jan. 22, 2013

(54) MOLECULES INVOLVED IN REGULATION OF OSTEOBLAST ACTIVITY AND OSTEOCLAST ACTIVITY, AND METHODS OF USE THEREOF

(75) Inventors: Laurie H. Glimcher, West Newton, MA (US); Dallas C. Jones, Brookline, MA (US); Antonios O. Aliprantis, Allston, MA (US)

(73) Assignee: Cornell University, Ithaca, NY (US)

( * ) Notice: Subject to any disclaimer, the term of this patent is extended or adjusted under 35 U.S.C. 154(b) by 1008 days.

(21) Appl. No.: 12/156,008

(22) Filed: May 29, 2008

(65) Prior Publication Data

US 2009/0053189 A1 Feb. 26, 2009

Related U.S. Application Data

(60) Provisional application No. 60/932,101, filed on May 29, 2007.

(51) Int. Cl.
*C40B 20/04* (2006.01)
*C12Q 1/68* (2006.01)
(52) U.S. Cl. ...... 506/4; 506/2; 506/7; 506/10; 435/7.23; 435/7.2; 435/4; 424/94.1
(58) Field of Classification Search .................. 506/4, 2, 506/7, 10; 435/7.23, 7.24; 424/94.1
See application file for complete search history.

(56) References Cited

U.S. PATENT DOCUMENTS

| 2003/0087259 A1* | 5/2003 | Clancy et al. ..................... 435/6 |
| 2003/0092603 A1 | 5/2003 | Mundy et al. |
| 2010/0055678 A1* | 3/2010 | Jaatinen et al. ................... 435/6 |
| 2010/0330085 A1* | 12/2010 | Coussens et al. .......... 424/133.1 |
| 2011/0008779 A1* | 1/2011 | Liew ................................. 435/6 |
| 2011/0183866 A1* | 7/2011 | Clarke et al. ..................... 506/9 |

FOREIGN PATENT DOCUMENTS

| WO | 00/77168 A2 | 12/2000 |
| WO | 01/16604 A1 | 3/2001 |
| WO | 02/086443 A2 | 10/2002 |
| WO | 2004/020458 A2 | 3/2004 |
| WO | 2005/113588 A2 | 12/2005 |
| WO | 2005/124343 A2 | 12/2005 |
| WO | 2006/113559 A2 | 10/2006 |
| WO | 2006/132248 A1 | 12/2006 |

OTHER PUBLICATIONS

Wu et al,Proceedings of the National Academy of Sciences of the United States of America (2008), 105(44), 16934-16939.*
Coquelle, Frederic M. et al., "Common and Divergent Roles for Members of the Mouse DCX Superfamily," Cell Cycle, vol. 5(9):976-983 (2006).
Glimcher, Laurie H. et al., "Control of Postnatal Bone Mass by the Zinc Finger ADapter Protein Schnurri-3," Ann. N.Y. Acad. Sci., vol. 1116:174-181 (2007).
Kaneki, Hiroyuki et al., "Tumor Necrosis Factor Promotes Runx2 Degradation through Up-regulation of Smurf1 and Smurf2 in Osteoblasts," J. Biol. Chem., vol. 281(7):4326-4333 (2006).
Mobasheri, A. et al., "Expression of Cation Exchange NHE and Anion Exchanger AE Isoforms in Primary Human Bone-Derived Osteoblasts," Cell Biology International, vol. 22(718):551-562 (1998).
Reiner, Orly et al., "The evolving doublecortin (DCX) superfamily," BMC Genomics, vol. 7(188) doi:10.1186/1471-2164-7-188 (2006).
International Search Report for Application No. PCT/US2008/006783, dated Dec. 9, 2008.
International Preliminary Report on Patentability and Written Opinion for Application No. PCT/US2008/006783, dated Dec. 1, 2009.

* cited by examiner

*Primary Examiner* — T. D. Wessendorf
(74) *Attorney, Agent, or Firm* — Nelson Mullins Riley & Scarborough LLP; Debra J. Milasincic, Esq.

(57) ABSTRACT

The present invention is based, at least in part, on the identification of molecules involved in the differentiation and/or activity of osteoblasts and osteoclasts. Accordingly, the present invention provides methods of identifying modulators of bone formation, mineralization, and/or osteoclastogenesis and methods for treating disorders that would benefit from modulation of bone formation, mineralization, and/or osteoclastogenesis using agents identified as described herein.

8 Claims, No Drawings

MOLECULES INVOLVED IN REGULATION OF OSTEOBLAST ACTIVITY AND OSTEOCLAST ACTIVITY, AND METHODS OF USE THEREOF

RELATED APPLICATIONS

This application claims priority to U.S. Provisional Application No. 60/932,101, filed May 29, 2008, titled "MOLECULES INVOLVED IN REGULATION OF OSTEOBLAST ACTIVITY AND OSTEOCLAST ACTIVITY, AND METHODS OF USE THEREOF", the entire contents of which is incorporated herein by this reference.

Government Support

This invention was made with government support under K08AR054859awarded by National Institutes of Health. The government has certain rights in the invention.

BACKGROUND OF THE INVENTION

Bone is a dynamic tissue whose matrix components are continuously being remodeled to preserve the structural integrity of the skeleton. Bone remodeling is a cyclical process where under normal physiological conditions, bone formation occurs only at sites where bone resorption has previously taken place. Homeostatic remodeling of the skeleton is mediated primarily, if not exclusively, by the osteoclast and the osteoblast (Erlebacher, A., et al. (1995). *Cell* 80, 371-378). Osteoclasts are giant multinucleated cells of hematopoietic origin that are responsible for bone resorption. Osteoblasts, which originate from mesenchymal stem cells, synthesize the matrix constituents on bone forming surfaces. Proliferation, differentiation and bone remodeling activities of these cells involve a complex temporal network of growth factors, signaling proteins, and transcription factors (Karsenty, G., and Wagner, E. F. (2002). *Dev Cell* 2, 389-406). Dysregulation of any one component may disrupt the remodeling process and contribute to the pathogenesis of certain skeletal disorders, such as osteoporosis and Paget's disease. Rare single gene disorders resulting in elevated bone mass due to osteoclast defects, collectively termed osteopetrosis, have been identified. Rarer are single gene disorders, exemplified by Camerati-Engelman syndrome, collectively termed osteoschlerosis, in which elevated bone mass is due to intrinsically-elevated osteoblast activity.

Currently available treatments for skeletal disorders and bone loss, whether targeted at bone formation by the osteoblast or bone resorption by the osteoclast, are inadequate. The scarcity of knowledge about the molecular and cellular targets in these cell types hinders the discovery of new therapeutics. Thus, further elucidation of the factors influencing osteoblast activity and/or osteoclast activity would be of value in identifying agents capable of modulating bone formation and mineralization. The identification of such agents and methods of using such agents would be of great benefit in the treatment of disorders that would benefit from increased or decreased bone formation.

SUMMARY OF THE INVENTION

The present invention is based, at least in part, on the identification of molecules involved in the differentiation and/or activity of osteoblasts and osteoclasts. In particular, an RNAi based screen has identified regulators of osteoblastogeneis and regulators of osteoclastogenesis.

Accordingly, in one aspect, the invention pertains to a method for increasing bone formation and mineralization, comprising providing an indicator composition comprising an osteoblast regulator selected from the group consisting of: TAOK2, DLG1, PIN1, LYK5, MOBKL2C, MAP4K2, PACSIN2, DCAMKL1, DOCK4, PARG1, TAOK3, TRPV6, CLK1, AAK1, PRKCA, AKAP8, DGKI, SMARCB1, CIB2, STK33, STK39, NRGN, PIK3R1, RASSF5, FRAP1, STK38, LATS1, LATS2, STK38L, GEFT, TNNI3K, STK4, RAF1, ARF1, C17orf31, EXO1, POT1, TERF2IP, MSH2, DKC1, MOBKL1A, MAP3K11, WWP2, and SMURF2, or biologically active fragments thereof, contacting the indicator composition with each member of a library of test compounds; and evaluating the expression and/or activity of the osteoblast regulator in the presence and absence of the test compound, to thereby identify a compound that increases bone formation and mineralization. In one embodiment, the indicator composition is a cellular composition. In another embodiment, the indicator composition is a cell free composition. In one embodiment, the osteoblast regulator is a positive regulator and the compound is identified as useful in increasing bone formation and mineralization by increasing the expression and/or activity of the regulator. In another embodiment, the osteoblast regulator is a negative regulator and the compound is identified as increasing bone formation and mineralization by decreasing the expression and/or activity of the regulator.

The invention also provides a method of identifying compounds useful in increasing bone formation and mineralization comprising, providing a mesenchymal stem cell comprising an osteoblast regulator selected from the group consisting of: TAOK2, DLG1, PIN1, LYK5, MOBKL2C, MAP4K2, PACSIN2, DCAMKL1, DOCK4, PARG1, TAOK3, TRPV6, CLK1, AAK1, PRKCA, AKAP8, DGKI, SMARCB1, CIB2, STK33, STK39, NRGN, PIK3R1, RASSF5, FRAP1, STK38, LATS1, LATS2, STK38L, GEFT, TNNI3K, STK4, RAF1, ARF1, C17orf1, EXO1, POT1, TERF2IP, MSH2, DKC1, MOBKL1A, MAP3K11, WWP2, and SMURF2, or biologically active portions thereof; contacting the cell with each member of a library of test compounds; and selecting from the library of test compounds a compound of interest that modulates the differentiation of the mesenchymal stem cell into an osteoblast to thereby identify a compound that increases bone formation and mineralization. In one embodiment, the osteoblast regulator is a positive regulator and the compound is identified as useful in increasing bone formation and mineralization by increasing the differentiation of the mesenchymal stem cell into an osteoblast. In another embodiment, the osteoblast regulator is a negative regulator and the compound is identified as increasing bone formation and mineralization by decreasing the differentiation of the mesenchymal stem cell into an osteoblast.

In another aspect, the invention provides a method of identifying compounds useful in increasing bone formation and mineralization comprising, providing an indicator composition comprising an osteoclast regulator selected from the group consisting of: GCK, WASF1, PPP2CB, PPP2R1A, CREBBP, CUL3, FBXW11, MELK, PLCL1, MAP3K3, DLGH1, NEK7, IRAK3, RHOC, SLC4A2, PLCB4, and B-RAF, BMPR2, MAPK3, and NHEDC2, or biologically active fragments thereof; contacting the indicator composition with each member of a library of test compounds; and evaluating the expression and/or activity of the osteoclast regulator in the presence and absence of the test compound, to thereby identify a compound that increases bone formation and mineralization. In one embodiment, the indicator composition is a cellular composition. In another embodiment, the indicator composition is a cell free composition. In one embodiment, the osteoclast regulator is a positive regulator and the compound is identified as useful in increasing bone formation and mineralization by decreasing the expression and/or activity of the regulator. In another embodiment, the osteoblast regulator is a negative regulator and the compound is identified as increasing bone formation and mineralization by increasing the expression and/or activity of the regulator.

The present invention also provides a method of identifying compounds useful in increasing bone formation and mineralization comprising, providing a hematopoietic stem cell comprising an osteoclast regulator selected from the group consisting of: GCK, WASF1, PPP2CB, PPP2R1A, CREBBP, CUL3, FBXW11, MELK, PLCL1, MAP3K3, DLGH1, NEK7, IRAK3, RHOC, SLC4A2, PLCB4, and B-RAF, BMPR2, MAPK3, and NHEDC2, or biologically active portions thereof; contacting the cell with each member of a library of test compounds; and selecting from the library of test compounds a compound of interest that modulates the differentiation of the hematopoietic stem cell into an osteoclast to thereby identify a compound that increases bone formation and mineralization. In one embodiment, the osteoclast regulator is a positive regulator and the compound is identified as useful in increasing bone formation and mineralization by decreasing the differentiation of the hematopoietic stem cell into an osteoclast. In another embodiment, the osteoblast regulator is a negative regulator and the compound is identified as increasing bone formation and mineralization by increasing the differentiation of the hematopoietic stem cell into an osteoclast.

In one embodiment of the methods of the invention, the indicator cell is an osteoblast. In one embodiment, the osteoblast is a mature osteoblast. In one embodiment, the indicator cell is a mesenchymal stem cell. In another embodiment, the indicator cell is an osteoclast. In one embodiment, the indicator cell is a hematopoietic stem cell.

In one embodiment of the methods of the invention, the indicator cell comprises a recombinant expression vector. In one embodiment, the recombinant expression vector is a lentiviral vector comprising an osteoclast regulator shRNA.

In one embodiment of the methods of the invention, the method is a high-throughput method. In one embodiment, the method is preformed in a 96-well format.

In one embodiment, the effect of the test compound of interest on mesenchymal stem cell differentiation is evaluated by determining the level of cellular alkaline phosphatase (ALP). In one embodiment, the effect of the test compound of interest on the level of cellular alkaline phosphatase (ALP) is evaluated by a colorimetric assay. In one embodiment, the methods of the invention further comprise normalizing cell number to the level of cellular alkaline phosphatase (ALP) by Alamar blue staining. In one embodiment, the methods of the invention further comprise evaluating the effect of the test compound of interest on mineralization. In one embodiment, evaluating the effect of the test compound of interest on mineralization is determined by xylenol orange staining.

In one embodiment, the methods of the invention further comprise determining the level of expression of at least one gene selected from the group consisting of: BSP, ColI($\alpha$)1, OCN, Osterix, RANKL, RSK2, RUNX2, Dlx-5, Msx-2, ALP, WWP1, and ATF4.

In one embodiment, the effect of the test compound of interest on hematopoietic stem cell differentiation is evaluated by determining the level of TRAP. In one embodiment, the effect of the test compound of interest on the level of TRAP is evaluated by a calorimetric assay. In one embodiment, the methods of the invention further comprise normalizing cell number to the level of TRAP by Alamar blue staining. In one embodiment, the methods of the invention further comprise evaluating the effect of the test compound of interest on the formation of resorption lacunae. In one embodiment, evaluating the effect of the test compound of interest on the formation of resorption lacunae is determined by von Kossa staining. In one embodiment, the methods of the invention further comprise determining the level of expression of at least one gene selected from the group consisting of: NFATc1, TRAP, Cathepsin K, MMP9, $\beta$3-integrin, and Calcitonin receptor.

In one embodiment, the methods of the invention further comprise determining the effect of the test compound of interest on bone formation and mineralization in a non-human adult animal, comprising administering the test compound to the animal and determining the effect of test compound on bone formation and mineralization in the presence and absence of the test compound, wherein an increase in bone formation and mineralization in the non-human animal identifies the test compound of interest as a compound that increases bone formation and mineralization. In one embodiment, the non-human animal is a mouse. In one embodiment, bone formation and mineralization is determined by measuring trabecular number. In another embodiment, the bone formation and mineralization is determined by measuring trabecular thickness. In another embodiment bone formation and mineralization is determined by measuring trabecular spacing. In yet another embodiment, bone formation and mineralization is determined by measuring bone volume. In one embodiment, bone formation and mineralization is determined by measuring volumetric bone mineral density. In another embodiment, bone formation and mineralization is determined by measuring trabecular number, measuring trabecular thickness, measuring trabecular spacing, measuring bone volume, and measuring volumetric bone mineral density. In one embodiment, the methods of the invention further comprise determining the serum levels of Trabp5b and deoxypyridinoline (Dpd).

In another aspect, the invention provides a method for increasing bone formation and mineralization, comprising contacting an osteoblast with an agent that decreases the expression and/or biological activity of a negative osteoblast regulator or a positive osteoclast regulator in the osteoblast such that bone formation and mineralization is increased.

Yet another aspect of the invention is a method for treating or preventing a disease, disorder, condition, or injury that would benefit from increased bone formation and mineralization in a subject, comprising contacting an osteoblast from the subject with an agent that decreases the expression and/or biological activity of a negative osteoblast regulator or a positive osteoclast regulator in the osteoblast such that the bone formation and mineralization in the subject is increased.

The invention also provides a method for decreasing bone formation and mineralization, comprising contacting an osteoblast with an agent that increases the expression and/or biological activity of a positive osteoblast regulator or a negative osteoclast regulator in the osteoblast such that bone formation and mineralization is decreased.

In another aspect, the invention provides a method for treating or preventing a disease, disorder, condition, or injury that would benefit from decreased bone formation and mineralization in a subject, comprising contacting an osteoblast from the subject with an agent that increases the expression and/or biological activity of a positive osteoblast regulator or a negative osteoclast regulator in the osteoblast such that the bone formation and mineralization in the subject is decreased.

In one embodiment, the step of contacting occurs in vitro. In another embodiment, the step of contacting occurs in vivo.

In one embodiment, the agent is present on a surface. In one embodiment, the disease, disorder, condition, or injury is selected from the group consisting of: osteoporosis, osteopenia, osteomalacia, and osteitis deformans (Paget's disease of bone). In another embodiment, the disease, disorder, condition, or injury is selected from the group consisting of: craniosynostosis and osteitis condensans.

DETAILED DESCRIPTION OF THE INVENTION

The present invention is based, at least in part, on the identification of molecules involved in the differentiation and/or activity of osteoclasts, i.e., molecules that participate in osteoclast differentiation. In particular, an RNAi based screen has identified both positive and negative regulators of osteoclastogenesis. The positive regulators of osteoclast differentiation that have been identified include, for example, GCK, WASF1, PPP2CB, PPP2R1A, CREBBP, MAP3K14 (NIK), CUL3, FBXW11, MELK, PLCL1, SYK, FRAP1, MAP3K3, DLGH1, NEK7, SFPI1 (Pu.1), IRAK3, IKBKB (IKKβ), RHOC, SLC4A2, PLCB4, and B-RAF. The negative regulators of osteoclast differentiation that have been identified include, for example, BMPR2, MAPK3, and NHEDC2.

The present invention is also based, at least in part, on the identification of molecules involved in the differentiation and/or activity of osteoblasts, i.e., molecules that participate in osteoblast differentiation. In particular, an RNAi based screen has identified negative regulators of osteoclastogenesis. The negative regulators of osteoblast differentiation that have been identified include, for example, TAOK2, DLG1, PIN1, LYK5, MOBKL2C, MAP4K2, PACSIN2, DCAMKL1, DOCK4, PARG1, TAOK3, TRPV6, CLK1, AAK1, PRKCA, AKAP8, DGKI, SMARCB1, CIB2, STK33, STK39, NRGN, PIK3R1, RASSF5, FRAP1, STK38, LATS1, LATS2, STK38L, GEFT, TNNI3K, STK4, RAF1, ARF1, C17orf31, EXO1, POT1, TERF2IP, MSH2, DKC1, MOBKL1A, MAP3K11, WWP2, and SMURF2.

Accordingly, the present invention provides methods of identifying modulators of bone formation and mineralization by modulating the expression and/or activity of these osteoblast or osteoclast regulators and methods for modulating bone formation and mineralization using agents that modulate the expression and/or activity of an osteoblast regulator and/or an osteoclast regulator.

Various aspects of the invention are described in further detail in the following subsections:

I. Definitions

As used herein, the term "bone formation and mineralization" refers to the cellular activity of osteoblasts to synthesize the collagenous precursors of bone extracellular matrix, regulate mineralization of the matrix to form bone, as well as their function in bone remodeling and reformation, e.g., bone mass is maintained by a balance between the activity of osteoblasts that form bone and the osteoclasts that break it down. Thus, as used herein, the term "bone formation and mineralization" also includes the cellular activity of osteoclasts to absorb and remove osseous tissue, i.e., osteoclastogenesis. The mineralization of bone occurs by deposition of carbonated hydroxyapatite crystals in an extracellular matrix consisting of type I collagen and a variety of non-collagenous proteins.

As used herein, an "osteoblast" is a bone-forming cell that is derived from mesenchymal osteoprogenitor cells and forms an osseous matrix in which it becomes enclosed as an osteocyte. A mature osteoblast is one capable of forming bone extracellular matrix in vivo, and can be identified in vitro by its capacity to form mineralized nodules which reflects the generation of extracellular matrix. An immature osteoblast is not capable of forming mineralized nodules in vitro.

As used herein, an "osteoclast" is a large multinucleated cell with abundant acidophilic cytoplasm derived from hematopoietic stem cells, functioning in the absorption and removal of osseous tissue. Osteoclasts become highly active in the presence of parathyroid hormone, causing increased bone resorption and release of bone salts (phosphorus and, especially, calcium) into the extracellular fluid. Osteoclasts are also identified based on the formation of actin ring structure and a polar cell body during resorption, and contraction in response to calcitonin. A mature osteoclast, but not its precursor cell, can be identified based on the secretion of the enzyme, Tartrate-resistant Acidic Phosphatase (TRAP).

As used herein, the term "osteoblast regulator" refers to a molecule described herein that has been identified as a regulator of osteoclastogenesis. A "positive osteoblast regulator" is one that results in the development of osteoblasts when its expression or activity is upregulated and thus, increase bone formation and mineralization. Downregulation of the expression and/or activity of a positive osteoblast regulator results in the inhibition of the development of osteoblasts and thus, decreased bone formation and mineralization. Conversely, a "negative osteoblast regulator" is a molecule that results in the increased development of osteoblasts when its expression or activity is downregulated and thus, increases bone formation and mineralization. Upmodulation of the expression and/or activity of a negative osteoblast regulator will result in the inhibition of the development of osteoblasts and thus, decreased bone formation and mineralization. Exemplary negative osteoblast regulators include, for example TAOK2, DLG1, PIN1, LYK5, MOBKL2C, MAP4K2, PACSIN2, DCAMKL1, DOCK4, PARG1, TAOK3, TRPV6, CLK1, AAK1, PRKCA, AKAP8, DGKI, SMARCB1, CIB2, STK33, STK39, NRGN, PIK3R1, RASSF5, FRAP1, STK38, LATS1, LATS2, STK38L, GEFT, TNNI3K, STK4, RAF1, ARF1, C17orf31, EXO1, POT1, TERF2IP, MSH2, DKC1, MOBKL1A, MAP3K11, WWP2, and SMURF2.

Similarly, the term "osteoclast regulator" refers to a molecule described herein that has been identified as a regulator of osteoclastogenesis. A "positive osteoclast regulator" is one that results in the decreased development of osteoclasts when its expression or activity is downregulated, thus, increasing bone formation and mineralization. Upmodulation of the expression and/or activity of a positive osteoclast regulator will result in increased development of osteoclasts and thus, decreased bone formation and mineralization. Conversely, a "negative osteoclast regulator" is a molecule that results in decreased osteoclastogenesis when its expression or activity is upregulated and thus increased bone formation and mineralization. Downmodulation of the expression and/or activity of a negative osteoclast regulator results in decreased development of osteoclasts and thus, increased bone formation and mineralization. Exemplary positive osteoclast regulators include, for example, GCK, WASF1, PPP2CB, PPP2R1A, CREBBP, MAP3K14 (NIK), CUL3, FBXW11, MELK, PLCL1, SYK, FRAP1, MAP3K3, DLGH1, NEK7, SFPI1 (Pu.1), IRAK3, IKBKB (IKKβ), RHOC, SLC4A2, PLCB4, and B-RAF. Exemplary negative osteoclast regulators include, for example, BMPR2, MAPK3, and NHEDC2.

In one embodiment, a regulator (osteoblast or osteoclast, positive or negative) is a kinase. In another embodiment, a regulator is a phosphatase. In another embodiment, a regulator is an ubiquitin ligase.

As used herein, the term "Gck", also referred to as "glucokinase (hexokinase 4, maturity onset diabetes of the young 2)", "EC 2.7.1.1", "GK", "GLK", "Glucokinase", "HHF3", "HK4", "HKIV", "HXKP", "Hexokinase-4", "Hexokinase-D", and "MODY2", refers to the structurally and functionally unique member of the family of enzymes called hexokinases, types I (142600) through IV (glucokinase). This family of enzymes catalyzes the phosphorylation of glucose at the sixth carbon position in the first step of glycolysis. Glucokinase is expressed only in mammalian liver and pancreatic islet beta cells. Because of its unique functional characteristics, the enzyme plays an important regulatory role in glucose metabolism. The rate of glucose metabolism in liver and pancreas is a function of the activity of the enzyme. Defects in the glucokinase gene have long been suspected contributors to the genetic susceptibility to noninsulin-dependent diabetes mellitus (NIDDM). For a review, see, for example, S. Baltrusch and M. Tiedge (2006) *Diabetes* 55:S55-S64.

There are three isoforms of human Gck, the amino acid sequences of which are known and can be found in, for example, GenBank accession numbers gi:4503951, gi:15967159, and gi:15967161. The nucleotide sequence of the three transcript variants of human Gck can be found in, for example, GenBank accession numbers gi:15967157, gi:15967158, and gi:15967160. The nucleotide and amino acid sequence of murine Gck can be found in, for example, GenBank accession number gi:118129970.

As used herein, the term "Wasf1", also referred to as "Wiskott-Aldrich syndrome protein family member 1", "WAS protein family, member 1", "FLJ31482", KIAA0269", "SCAR1", "WAVE", and "WAVE1", refers to a downstream effector molecule involved in the transmission of signals from tyrosine kinase receptors and small GTPases to the actin cytoskeleton. The transmission of such signals is critical to cell morphological changes and motility. For a review, see, for example, Higgs and Pollard (2001) *Annu Rev Biochem.* 70:649-76.

There are four isoforms of human Wasf1, the amino acid sequences of which are known and can be found in, for example, GenBank accession numbers gi:68161500, gi:68161502, gi:68161504, and gi:4507913. The nucleotide sequence of the four transcript variants of human Wasf1 can be found in, for example, GenBank accession numbers gi:68161499, gi:68161501, gi:68161503, and gi:68161486. The nucleotide and amino acid sequence of murine Wasf1 can be found in, for example, Genbank accession number gi:31982605.

As used herein, the term "Ppp2cb", also referred to as "protein phosphatase 2 (formerly 2A, catalytic subunit, beta isoform", "EC 3.1.3.16", "PP2A-beta", and "PP2CB", refers to the beta subunit of protein phosphatase 2. Protein phosphatase 2 is one of the four major serine/threonine phosphatases, which is involved in the negative control of cell growth and division. It consists of a common heteromeric core enzyme, which is composed of a catalytic subunit and a constant regulatory subunit, which associates with a variety of regulatory subunits. The Ppp2cb gene encodes a beta isoform of the catalytic subunit. See, for example, Zhou, J., et al. (2003) *Biochem J.* 369(Pt 2):387-98.

There are two isoforms of human Ppp2cb, the amino acid sequences of which are known and can be found in, for example, GenBank accession numbers gi:57222565 and gi:4758952. The nucleotide sequence of the two transcript variants of human Ppp2cb can be found in, for example, GenBank accession numbers gi:57222564 and gi:57634540. The nucleotide and amino acid sequence of murine Ppp2cb can be found in, for example, GenBank accession number gi:119672926.

As used herein, the term "Ppp2r1a", also referred to as "protein phosphatase 2 (formerly 2A), regulatory subunit A, alpha isoform", "MGC786", and "PR65A", refers to the constant regulatory subunit of protein phosphatase 2. Protein phosphatase 2 is one of the four major serine/threonine phosphatases which is involved in the negative control of cell growth and division. It consists of a common heteromeric core enzyme, which is composed of a catalytic subunit and a constant regulatory subunit, which associates with a variety of regulatory subunits. The constant regulatory subunit A serves as a scaffolding molecule to coordinate the assembly of the catalytic subunit and a variable regulatory B subunit. The Ppp2r1a gene encodes the alpha isoform of the constant regulatory subunit A.

The amino acid sequence of human Ppp2r1a is known and can be found in, for example, GenBank accession number gi:21361399. The nucleotide sequence of human Ppp2r1a can be found in, for example, GenBank accession number gi:32455242. The nucleotide and amino acid sequence of murine Ppp2cb can be found in, for example, GenBank accession number gi: 118131166.

As used herein, the term "Crebbp" also referred to as "CREB binding protein (Rubinstein-Taybi syndrome)", "CBP", "EC 2.3.1.48", "RSTS", and "RTS" refers to the art known transcriptional coactivator of RNA polymerase II-mediated transcription. For a review, see, for example, Johannessen, M., et al. (2004) *Cell Signal.* 16(11):1211-27.

There are two isoforms of human Crebbp, the amino acid sequences of which are known and can be found in, for example, GenBank accession numbers gi:119943102 and gi:119943104. The nucleotide sequence of the two transcript variants of human Crebbp can be found in, for example, GenBank accession numbers gi:119943101 and gi:119943103. The nucleotide and amino acid sequence of murine Crebbp can be found in, for example, GenBank accession number gi:70995310.

As used herein, the term "Map3k14", also referred to as "mitogen-activated protein kinase kinase kinase 14", "EC 2.7.11.25", "FTDCR1B", "HS", "HSNIK", "HsNIK, and "NIK", refers to the art recognized serine/threonine kinase which is involved in the activation of transcription factor NF-kappa-B in response to TNF-alpha, IL1, and FAS antigen and binds to the signal transducer, TRAF2. See, for example, Malinin N L et al MAP3K-related kinase involved in NF-kappaB induction by TNF, CD95 and IL-1. Nature 385: 540-544 (1997); Matsushima A et al Essential role of nuclear factor (NF)-kappa-B-inducing kinase and inhibitor of kappa-B (1-kappa-B) kinase alpha in NF-kappa-B activation through lymphotoxin beta receptor, but not through tumor necrosis factor receptor I. Journal of Experimental Medicine 193: 631-636 (200%); Yin L et al Defective lymphotoxin-beta receptor-induced NF-kappa-B transcriptional activity in NIK-deficient mice. Science 291: 2162-2165 (2001).

The amino acid sequence of human Map3k14 is known and can be found in, for example, GenBank accession number gi:115298645. The nucleotide sequence of human Map3k14 can be found in, for example, GenBank accession number gi:115298644. The nucleotide and amino acid sequence of murine Map3k14 can be found in, for example, GenBank accession number gi:142388182.

As used herein, the term "Cul3", also referred to as "cullin 3", and "KIAA0617" refers to the member of the SCF (Skp1-Cullin-F-box) E3 ubiquitin ligase family which target substrates for ubiquitin-dependent degradation by the 26S proteasome. For reviews, see, for example, Willems A R, et al. (2004) *Biochim Biophys Acta.* 1695(1-3):133-70 and Pintard L, et al. (2004) *EMBO J.* 23(8):1681-7.

The amino acid sequence of human Cul3 is known and can be found in, for example, GenBank accession number gi:4503165. The nucleotide sequence of human Cul3 be found in, for example, GenBank accession number gi:45827792. The nucleotide and amino acid sequence of murine Cul3 may be found in, for example, GenBank accession number gi:142388897.

As used herein, the term "Fbxw11", also referred to as "F-box and WD repeat domain containing 11", "BTRC2", "BTRCP2", "FBW1B", "FBXW1B", "Fbw11", "Fbw1b", "Hos, and "KIAA0696", refers to the component of the modular E3 ubiquitin protein ligases called SCFs (SKP1, cullin, which function in phosphorylation-dependent ubiquitination. See, e.g., Suzuki H, et al. (1999) *Biochem Biophys Res Commun.* 5; 256(1):127-32.

There are three isoforms of human Fbxw11, the amino acid sequences of which are known and can be found in, for example, GenBank accession numbers gi:48928050, gi:48928046, and gi:48928048. The nucleotide sequence of the three transcript variants of human Fbxw11 can be found in, for example, GenBank accession numbers gi:48928049, gi:48928045, and gi:48928047. The nucleotide and amino acid sequence of murine Fbxw11 can be found in, for example, GenBank accession number gi:118129917.

As used herein, the term "Melk", also referred to as "maternal embryonic leucine zipper kinase", "EC 2.7.11.1", "HPK38", "KIAA0175", "OTTHUMP0000046113", "hMELK", and "hPK38", refers to the art recognized serine/threonine kinase which is involved in stem cell renewal, cell cycle progression, and pre-mRNA splicing. See, for example, Beullens M, et al. (2005) *J Biol Chem.* 280(48):40003-11.

The amino acid sequence of human Melk is known and can be found in, for example, GenBank accession number gi:7661974. The nucleotide sequence of human Melk be found in, for example, GenBank accession number gi:41281490. The nucleotide and amino acid sequence of murine Melk may be found in, for example, GenBank accession number gi:31981625.

As used herein, the term "Plcl1", also referred to as "phospholipase C-like 1", "MGC126580", "MGC138190", "PLC-L", "PLCE", "PLCL", and "PLDL1" refers to a molecule which was shown to be homozygously deleted in human small cell lung carcinoma. The homology of Plcl1 to phospholipase C genes indicates that it is involved in an inositol phospholipid-based intracellular signaling cascade. See, for example, Kohno et al. (1995) *Hum. Molec. Genet.* 4: 667-674.

The amino acid sequence of human Plcl1 is known and can be found in, for example, GenBank accession number gi:5453912. The nucleotide sequence of human Plcl1 be found in, for example, GenBank accession number gi:5453911. The nucleotide and amino acid sequence of rat Plcl1 may be found in, for example, GenBank accession number gi:16758195.

As used herein, the term "Frap1", also referred to as "FK506 binding protein 12-rapamycin associated protein 1", "FLJ44809", "FRAP", "FRAP2", "MTOR", "RAFT1", RAPT1", and "mTOR" refers to one of a family of phosphatidylinositol kinase-related kinases which mediate cellular responses to stresses such as DNA damage and nutrient deprivation. This protein acts as the target for the cell-cycle arrest and immunosuppressive effects of the FKBP12-rapamycin complex. See, for example, Findlay G M, et al. (2007) *Biochem J.* 403(1):13-20.

The amino acid sequence of human Frap1 is known and can be found in, for example, GenBank accession number gi:4826730. The nucleotide sequence of human Frap1 be found in, for example, GenBank accession number gi:19924298. The nucleotide and amino acid sequence of mouse Frap1 may be found in, for example, GenBank accession number gi:9910227.

As used herein, the term "Map3k3", also referred to as "mitogen-activated protein kinase kinase kinase 3", "EC 2.7.11.25", "MAPKKK3", and "MEKK3" refers to a molecule that belongs to the Mekk/Ste11 family of serine/threonine kinases and is a member of the MAP-kinase signaling cascade that activates and phosphorylates the kinase MEK5 in response to growth factors, oxidative stress, and hyperosmotic conditions. MEKK3 directly regulates the stress-activated protein kinase (SAPK) and extracellular signal-regulated protein kinase (ERK) pathways by activating SEK and MEK1/2. Moreover, MEKK3 is crucial for IL 1-R and TLR4 signaling through the IKK—NFkB and JNK-p38 MAPK pathways. See, for example, Ellinger-Ziegelbauer, H., et al. (1997). *J. Biol. Chem.* 272: 2668-2674.

There are two isoforms of human Map3k3, the amino acid sequences of which are known and can be found in, for example, GenBank accession numbers gi:42794765 and gi:42794767. The nucleotide sequence of the two transcript variants of human Map3k3 can be found in, for example, GenBank accession numbers gi:42794764 and gi:42794766. The nucleotide and amino acid sequence of murine Map3k3 can be found in, for example, GenBank accession number gi:142362504.

As used herein, the term "Dlgh1", also referred to as "discs, large homolog 1 (Drosophila)", "DKFZp761P0818", "DLGH1", "SAP-97", "SAP97", "dJ1061C18.1.1", "hDlg", and "hdlg" refers to the human homolog of the *Drosophila* lethal (1) discs larige-1 (dlg) tumor suppressor. See, for example, Round J L, et al. (2007) *Nat Immunol.* 8(2):154-61.

The amino acid sequence of human Dlgh1 is known and can be found in, for example, GenBank accession number gi:4758162. The nucleotide sequence of human Dlgh1 be found in, for example, GenBank accession number gi:4758161. The nucleotide and amino acid sequence of mouse Dlgh1 may be found in, for example, GenBank accession number gi:40254641.

As used herein, the term "Nek7", also referred to as "NIMA (never in mitosis gene a)-related kinase 7", and "EC 2.7.11.1" refers to a serine/threonine protein kinase that shares high amino acid sequence identity with the gene product of the *Aspergillus nidulans* 'never in mitosis A' gene, which controls initiation of mitosis. See, for example, Belham C, et al. (2003) *J Biol. Chem.* 12; 278(37):34897-909.

The amino acid sequence of human Nek7 is known and can be found in, for example, GenBank accession number gi:19424132. The nucleotide sequence of human Nek7 be found in, for example, GenBank accession number gi:19424131. The nucleotide and amino acid sequence of mouse Nek7 may be found in, for example, GenBank accession number gi:118130435.

As used herein, the term "Irak3", also referred to as "interleukin-1 receptor-associated kinase 3", "IRAK-3", and "IRAK-M" refers to a serine/threonine protein kinase of the Interleukin (IL)-1 receptor (IL-1R)-associated kinase family. See, for example, Li H, et al. (2005) *J Exp Med.* 201(7):1169-77.

The amino acid sequence of human Irak3 is known and can be found in, for example, GenBank accession number gi:6005792. The nucleotide sequence of human Irak3 can be found in, for example, GenBank accession number gi:6005791. The nucleotide and amino acid sequence of mouse Irak3 may be found in, for example, GenBank accession number gi:142380077.

As used herein, the term "B-raf", also referred to as "BRAF1", "EC 2.7.11.1", "MGC126806", "MGC138284", "RAFB1", and p94 refers to the serine/threonine protein kinase implicated in numerous cancers. See, for example, Chadee D N, et al. (2006) *Proc Natl Acad Sci USA.* 2006 103(12):4463-8.

The amino acid sequence of human B-raf is known and can be found in, for example, GenBank accession number gi:33188459. The nucleotide sequence of human B-raf be found in, for example, GenBank accession number gi:90265828. The nucleotide and amino acid sequence of rat B-raf may be found in, for example, GenBank accession number gi:109471940.

As used herein, the term "Bmpr2", also referred to as "bone morphogenetic protein receptor, type II (serine/threonine kinase)", "BMPR-II", "BMPR3", "BMR2", "BRK-3", "EC 2.7.11.30", "PPH1", and "T-ALK" refers to a member of the bone morphogenetic protein (BMP) receptor family of transmembrane serine/threonine kinases. The ligands of this receptor are BMPs, which are members of the TGF-beta superfamily. BMPs are involved in endochondral bone formation and embryogenesis. These proteins transduce their signals through the formation of heteromeric complexes of 2 different types of serine (threonine) kinase receptors: type I receptors of about 50-55 kD and type II receptors of about 70-80 kD. Type II receptors bind ligands in the absence of type I receptors, but they require their respective type I receptors for signaling, whereas type I receptors require their respective type II receptors for ligand binding. Mutations in this gene have been associated with primary pulmonary hypertension.

The amino acid sequence of human Bmpr2 is known and can be found in, for example, GenBank accession number gi:15451916. The nucleotide sequence of human Bmpr2 be found in, for example, GenBank accession number gi:72376969. The nucleotide and amino acid sequence of rat Bmpr2 may be found in, for example, GenBank accession number gi:145966831.

As used herein, the term "Mapk3", also referred to as "mitogen-activated protein kinase 3", "EC 2.7.11.24", "ERK-1", "ERK1", "ERT2", "HS44 KDAP", "HUMKER1A", "MGC20180", "P44ERK1", "P44MAPK", "PRKM3", "p44-ERK1", "p44-MAPK", "p44erk1", and "p44mapk, refers to the sertine/threonine kinase that is involved in both the initiation and regulation of meiosis, mitosis, and postmitotic functions in differentiated cells by phosphorylating a number of transcription factors such as ELK-1. Phosphorylates EIF4EBP1; required for initiation of translation. Phosphorylates microtubule-associated protein 2 (MAP2). See, Todd J L, et al. (1999) *J Biol. Chem.* 274(19): 13271-80.

There are two isoforms of human Mapk3, the amino acid sequences of which are known and can be found in, for example, GenBank accession numbers gi:91718897 and gi:91718899. The nucleotide sequence of the two transcript variants of human Mapk3 can be found in, for example, GenBank accession numbers gi:91718896 and gi:91718898. The nucleotide and amino acid sequence of murine Mapk3 can be found in, for example, GenBank accession number gi:93102422.

As used herein, the term "MOBKL1A", also referred to as "MOB1, Mps One Binder kinase activator-like 1A (yeast)", "MATS2", "MGC339", "MOB4A", "Mob1A", and "Mob1B", refers to the human ortholog of the *Drosophila* protein belonging to the Mob1 superfamily termed Mats (Mob as tumor suppressor). In *Drosophila*, Mats functions as a growth inhibitor and loss of Mats function results in increased cell proliferation, defective apoptosis, and induction of tissue overgrowth. See, e.g., Lai, Z.-C et al. Cell 120: 675-685, 2005. In mammals, Mob1 is a regulator of mitotic exit (a mitotic checkpoint gene), associates with Lats2 to induce its activation. See, for example, Sasaki H, et al. (2007) Clin Lung Cancer. 8(4):273-6.

The amino acid sequence of human MOBKL1A is known and can be found in, for example, GenBank accession number gi:27735029. The nucleotide sequence of human MOBKL1A can be found in, for example, GenBank accession number gi:41406062. The nucleotide and amino acid sequence of murine MOBKL1A can be found in, for example, GenBank accession number gi:118600996.

As used herein, the term "DKC1", also referred to as "dyskeratosis congenita 1", "dyskerin", "EC 5.4.99", "NAP57", "NOLA4", and "XAP101", refers to the nuclear protein which is the catalytic subunit of H/ACA small nucleolar ribonucleoprotein (H/ACA snoRNP) complex, which catalyzes pseudouridylation of rRNA and is required for ribosome biogenesis and telomere maintenance, for correct processing or intranuclear trafficking of TERC, the RNA component of the telomerase reverse transcriptase (TERT) holoenzyme.

The amino acid sequence of human DKC1 is known and can be found in, for example, GenBank accession number gi:4503337. The nucleotide sequence of human DKC1 can be found in, for example, GenBank accession number gi:15011921.

As used herein, the term "MSH2" also referred to as "mutS homolog 2", "colon cancer, nonpolyposis type 1 (*E. coli*)", "COCA1", "FCC1", "HNPCC", and "HNPCC1" is homologous to the *E. coli* MutS gene and is involved in DNA mismatch repair. Mutations in the MSH2 gene result in hereditary nonpolyposis colorectal cancer-1.

The amino acid sequence of human MSH2 is known and can be found in, for example, GenBank accession number gi:4557761. The nucleotide sequence of human MSH2 can be found in, for example, GenBank accession number gi:4557760. The nucleotide and amino acid sequence of murine MSH2 can can be found in, for example, GenBank accession number gi: 118130707.

As used herein, the term "TERF2IP", also referred to as "telomeric repeat binding factor 2, interacting protein", "DRIP5", "RAP1", and "hRap1" refers to the protein recruited to telomeres by but does not directly bind to DNA itself. See, Li, B.; Oestreich, S.; de Lange, T. Cell 101: 471-483, 2000.

The amino acid sequence of human TERF2IP is known and can be found in, for example, GenBank accession number gi:52627149. The nucleotide sequence of human TERF2IP can be found in, for example, GenBank accession number gi:52627148. The nucleotide and amino acid sequence of murine TERF2IP can can be found in, for example, GenBank accession number gi:15618998.

As used herein, the term "POT1" also referred to as "POT1 protection of telomeres 1 homolog (*S. pombe*)", "DKFZP586D211", "DKFZp586D211", and "hPot1" refers to the protein conserved across widely diverged eukaryotes that binds the G-rich strand of its own telomeric repeat sequence, thus protecting chromosome ends. See, Baumann, P.; Cech, T. R. Science 292: 1171-1175, 2001.

There are two isoforms of human POT1, the amino acid sequences of which are known and can be found in, for example, GenBank accession numbers gi:110671314 and gi:98991776. The nucleotide sequence of the two transcript variants of human POT1 can be found in, for example, GenBank accession numbers gi:110671313 and gi:98991775.

The nucleotide and amino acid sequence of murine POT1 can be found in, for example, GenBank accession number gi:146149244.

As used herein, the term "EXO1" also referred to as "exonuclease 1", and "HEX1" refers to the member of the RAD2 nuclease family and functions in DNA replication, repair, and recombination with exonuclease activity with a 5-prime-to-3-prime polarity. See, Genschel, J.; Bazemore, L. R.; Modrich, P. J. Biol. Chem. 277: 13302-13311, 2002.

There are three isoforms of human EXO1, the amino acid sequences of which are known and can be found in, for example, GenBank accession numbers gi:39995069, gi:39995071, and gi:18491016. The nucleotide sequence of the three transcript variants of human EXO1 be found in, for example, GenBank accession numbers gi:39995068, gi:39995070, and gi:39995067. The nucleotide and amino acid sequence of murine EXO1 can be found in, for example, GenBank accession number gi:141801186.

As used herein, the term "C17orf3", also referred to as "SMG6", "Smg-6 homolog, nonsense mediated mRNA decay factor (C. elegans)", "EST 1A", "Est1p-like", "KIAA0732", "SMG-6", and "hSmg5/7" refers to the component of the telomerase ribonucleoprotein complex which interacts with TERT, independently of the telomerase RNA. C17orf31 binds to the single-stranded 5'-(GTGTGG)(4) GTGT-3' telomeric DNA, but not to a telomerase RNA template component (TER). It also interacts with PP2A catalytic subunits, SMG1, RENT1, RENT2 and RENT3B. See, Fukuhara, N.; at al. Molec. Cell 17: 537-547, 2005.

The amino acid sequence of human C17orf31 is known and can be found in, for example, GenBank accession number gi: 115511020. The nucleotide sequence of human C17 orf31 can be found in, for example, GenBank accession number gi:115511019. The nucleotide and amino acid sequence of murine C17orf31 can can be found in, for example, GenBank accession number gi:50582544.

As used herein, the term "ARF1", also referred to as "ADP-ribosylation factor 1" refers to one member of the Ras family of proteins that is a GTP-binding protein that functions as an allosteric activator of the cholera toxin catalytic subunit, an ADP-ribosyltransferase. It is involved in protein trafficking among different compartments, modulates vesicle budding and uncoating within the Golgi complex. The hydrolysis of ARF1-bound GTP, which is mediated by ARFGAPs proteins, is required for dissociation of coat proteins from Golgi membranes and vesicles. See, Gillingham A, Munro S. Annu Rev Cell Dev Biol. 2006.

There are four isoforms of human ARF1, the amino acid sequences of which are known and can be found in, for example, GenBank accession numbers gi:66879660, gi:66879662, gi:66879664, and gi:4502201. The nucleotide sequence of the four transcript variants of human ARF1 can be found in, for example, GenBank accession numbers gi:66879659, gi:66879661, gi:66879663, and gi:66879658. The nucleotide and amino acid sequence of murine ARF1 can be found in, for example, GenBank accession number gi:31560734.

As used herein, the term "RAF1", also referred to as "v-raf-1 murine leukemia viral oncogene homolog 1", and c-raf" refers to the protein that interacts with Ras proteins, which is antagonized by RIN1. RAF1 counteracts apoptosis by suppressing the activation of mammalian sterile 20-like kinase. RAF1 prevents dimerization and phosphorylation of the activation loop of MST2 independently of its protein kinase activity. Depletion of MST2 from Raf1-null mouse or human cells abrogated sensitivity to apoptosis, whereas overexpression of MST2 induced apoptosis. Conversely, depletion of Raf1 from Raf1+/+mouse or human cells led to MST2 activation and apoptosis. The concomitant depletion of both RAF1 and MST2 prevented apoptosis. See, O'Neill, E.; et al. Science 306: 2267-2270, 2004.

The amino acid sequence of human RAF1 is known and can be found in, for example, GenBank accession number gi:4506401. The nucleotide sequence of human RAF1 can be found in, for example, GenBank accession number gi:52486392. The nucleotide and amino acid sequence of murine RAF1 can be found in, for example, GenBank accession number gi:14238003.

As used herein, the term "STK4", also referred to as "serine/threonine kinase 4", "DKFZp686A2068", "EC 2.7.11.1", "KRS2", "MST-1", MST1", and "YSK3" refers to the stress-activated, pro-apoptotic kinase which, following caspase-cleavage, enters the nucleus and induces chromatin condensation followed by internucleosomal DNA fragmentation. STK4 phosphorylates 'Ser-14' of histone H2B during apoptosis. Phosphorylates FOXO3 upon oxidative stress, which results in its nuclear translocation and cell death initiation. See, Lehtinen M K, et al. Cell. 2006 125(5):987-1001.

The amino acid sequence of human STK4 is known and can be found in, for example, GenBank accession number gi:5454096. The nucleotide sequence of human STK4 can be found in, for example, GenBank accession number gi:38327560. The nucleotide and amino acid sequence of murine STK4 can be found in, for example, GenBank accession number gi:142361509.

As used herein, the term "TNNI3K", also referred to as "TNNI3 interacting kinase", "CARK", "EC 2.7.11.1", "MGC142099", and "MGC33828" refers to the member of the Ser/Thr protein kinase family, and the MAP kinase kinase kinase subfamily which is a cardiac-specific kinase and play important roles in cardiac system. See,: Zhao Y, et al. J Mol Med. 2003 May; 81(5):297-304.

The amino acid sequence of human TNNI3K is known and can be found in, for example, GenBank accession number gi:7705748. The nucleotide sequence of human TNNI3K can be found in, for example, GenBank accession number gi:7705747. The nucleotide and amino acid sequence of murine TNNI3K can be found in, for example, GenBank accession number gi: 142364382.

As used herein, the term "GEFT", also referred to as "RAC/CDC42 exchange factor", and "p63RhoGEF" refers to the guanine nucleotide exchange factor that activatesRho GTPases by accelerating GDP/GTP exchange, thus inducing cell proliferation, transformation, and migration. See, Guo X, et al. J Biol Chem. 2003 Apr. 11; 278(15):13207-15.

There are two isoforms of human GEFT, the amino acid sequences of which are known and can be found in, for example, GenBank accession numbers gi:19311008 and gi:33667115. The nucleotide sequence of the two transcript variants of human GEFT can be found in, for example, GenBank accession numbers gi:19311007 and gi:33667114. The nucleotide and amino acid sequence of murine GEFT can be found in, for example, GenBank accession number gi:142362982.

As used herein, the term "STK38L", also referred to as "serine/threonine kinase 38 like", "KIAA0965", and "NDR2" refers to the member of the Ser/Thr protein kinase family STK38L is also referred to as a Nuclear Dbf2-related (NDR) protein kinase which is a family of AGC group kinases that are involved in the regulation of cell division and cell morphology. SB100 stimulates autophosphorylation of STK38L. See, Stegert M R, et al. J Biol Chem. 2004; 279 (22):23806-12.

The amino acid sequence of human STK38L is known and can be found in, for example, GenBank accession number gi:24307971. The nucleotide sequence of human STK38L can be found in, for example, GenBank accession number gi:142386223. The nucleotide and amino acid sequence of murine STK38L can be found in, for example, GenBank accession number gi:31982109.

As used herein, the term "LATS2", also referred to as "LATS, large tumor suppressor, homolog 2 (Drosophila)", "FLJ13161", and "KPM" refers to the serine/threonine kinase that interacts physically with MDM2 to inhibit p53 ubiquitination and to promote p53 activation. It also interacts with and is phosphorylated by STK6. LATS is also a tumor suppressor which plays a critical role in centrosome duplication, maintenance of mitotic fidelity and genomic stability and negatively regulates G1/S transition by down-regulating cyclin E/CDK2 kinase activity. Negative regulator of the androgen receptor. See, Aylon Y, et al. Genes Dev. 2006 20(19):2687-700.

The amino acid sequence of human LATS2 is known and can be found in, for example, GenBank accession number gi:126507091. The nucleotide sequence of human LATS2 can be found in, for example, GenBank accession number gi:126507090. The nucleotide and amino acid sequence of murine LATS2 can be found in, for example, GenBank accession number gi:68448548.

As used herein, the term "LATS1", also referred to as "LATS, large tumor suppressor, homolog 1 (*Drosophila*)", "WARTS", "h-warts", and "wts" refers to the Ser/Thr protein kinase family member which is a tumor suppressor which plays a critical role in maintenance of ploidy through its actions in both mitotic progression and the G1 tetraploidy checkpoint. Negatively regulates G2/M transition by down-regulating CDC2 kinase activity. Involved in the control of p53 expression. Affects cytokinesis by regulating actin polymerization through negative modulation of LIMK1. See, Yang X, et al. Nat Cell Biol. 2004 6(7):609-17.

The amino acid sequence of human LATS1 is known and can be found in, for example, GenBank accession number gi:4758666. The nucleotide sequence of human LATS1 can be found in, for example, GenBank accession number gi:10862687. The nucleotide and amino acid sequence of murine LATS1 can be found in, for example, GenBank accession number gi:94387911.

As used herein, the term "STK38", also referred to as "serine/threonine kinase 38", and "NDR1" refers to the kinase that playa a role in growth arrest and cell differentiation, possibly as a signaling protein shuttling between the cytoplasm and the nucleus. Kalaydjieva et al. (2000) Hum. J. Hum. Genet. 67: 47-58, 2000) demonstrated that expression in peripheral nerve is particularly high in Schwann cells. Taken together, the findings show that STK38 plays a role in the peripheral nervous system in Schwann cell signaling necessary for axonal survival.

The amino acid sequence of human STK38 is known and can be found in, for example, GenBank accession number gi:6005814. The nucleotide sequence of human STK38 can be found in, for example, GenBank accession number gi:31377778. The nucleotide and amino acid sequence of murine STK38 can be found in, for example, GenBank accession number gi: 118129944.

As used herein, the term "RASSF5", also referred to as "Ras association (RalGDS/AF-6) domain family 5", "MGC10823", "MGC17344", "Maxp1", "NORE1", "NORE1A", "NORE1B", "RAPL", and "RASSF3" refers to the protein involved in lymphocyte adhesion by linking RAP1A activation upon T cell receptor or chemokine stimulation to integrin activation. Isoform 2 stimulates lymphocyte polarization and the patch-like distribution of ITGAL/LFA-1, resulting in an enhanced adhesion to ICAM1. Together with RAP1A RASSF5 participates in regulation of microtubule growth. The association of isoform 2 with activated RAP1A is required for directional movement of endothelial cells during wound healing. May be involved in regulation of Ras apoptotic function, and The RASSF5-STK4 complex mediates HRAS1 and KRAS induced apoptosis. See Praskova M, et al. Biochem J. 2004 Jul. 15; 381(Pt 2):453-62.

There are four isoforms of human RASSF5, the amino acid sequences of which are known and can be found in, for example, GenBank accession numbers gi:13899265, gi:32996731, gi:32996733, and gi:32996735. The nucleotide sequence of the four transcript variants of human RASSF5 can be found in, for example, GenBank accession numbers gi:13899264, gi:115430205, gi:115430204, and gi:115430207. The nucleotide and amino acid sequence of murine RASSF5 can be found in, for example, Genbank accession number gi:141803301.

"Bone sialoprotein" or "BSP" is belongs to the osteopontin gene family and is a non-collagenase bone matrix protein that binds tightly to hydroxyapatite, forming an integral part of the mineralized matrix of bone. The nucleotide sequence and amino acid sequence of human BSP, is described in, for example, GenBank Accession No. gi:38146097. The nucleotide sequence and amino acid sequence of murine BSP, is described in, for example, GenBank Accession No. gi:6678112.

Type I collagen (α)1 ("CoII(α)1"), is a collagenase bone matrix protein. The nucleotide sequence and amino acid sequence of human CoII(α)1, is described in, for example, GenBank Accession No. gi:14719826. The nucleotide sequence and amino acid sequence of murine CoII(α)1, is described in, for example, GenBank Accession No. gi:34328107.

OCN, also referred to as osteocalcin and bone gamma-carboxyglutamic acid (Gla) protein (BGLAP, or BGP) is a small, highly conserved molecule associated with the mineralized matrix of bone. It is a noncollagenous protein found in bone and dentin. It is secreted by osteoblasts and plays a role in mineralization and calcium ion homeostasis. The nucleotide sequence and amino acid sequence of human OCN, is described in, for example, GenBank Accession No. gi:158517828. The nucleotide sequence and amino acid sequence of murine OCN, is described in, for example, GenBank Accession No gi:83816951.

Rsk2, also referred to as Ribosomal Protein S6 Kinase, 90-KD, 3; RPS6KA3, is a member of the RSK (ribosomal S6 kinase) family of growth factor-regulated serine/threonine kinases, known also as p90(rsk). The highly conserved feature of all members of the RSK family is the presence of 2 nonidentical kinase catalytic domains. RSK2 is required for osteoblast differentiation and function. ATF4 is a critical substrate of RSK2 that is required for the timely onset of osteoblast differentiation, for terminal differentiation of osteoblasts, and for osteoblast-specific gene expression. Additionally, RSK2 and ATF4 posttranscriptionally regulate the synthesis of type I collagen. The nucleotide sequence and amino acid sequence of human RSK2, is described in, for example, GenBank Accession No. gi:56243494. The nucleotide sequence and amino acid sequence of murine Rsk2, is described in, for example, GenBank Accession No gi:22507356.

Runx2, also referred to as Runt-related transcription factor 2, CBFA1 encodes a protein with a highly conserved runt domain. Cbfa1 binds to an osteoblast-specific cis-acting element, termed OSE2, in the promoter of osteocalcin. Cbfa1 is an osteoblast-specific transcription factor and a regulator of osteoblast differentiation. There are three isoforms of human Runx2, the amino acid sequences and nucleotide sequences of which are known and can be found in, for example, GenBank accession numbers gi:116734652], gi:116734654, and gi:66934968. The nucleotide sequence and amino acid sequence of murine Runx2, is described in, for example, GenBank Accession No gi:148747264.

ALP also referred to as PDLIM3, Actinin-associated LIM protein binds to the spectrin-like motifs of alpha-actinin-2 in skeletal muscle. The nucleotide sequence and amino acid sequence of human ALP, is described in, for example, GenBank Accession No. gi:166235175. The nucleotide sequence and amino acid sequence of murine Alp, is described in, for example, GenBank Accession gi:47125033.

WWP1, also referred to as WW domain containing E3 ubiquitin protein ligase 1. WW domain-containing proteins encodes a protein which contains 4 tandem WW domains and a HECT (homologous to the E6-associated protein carboxyl terminus) domain. The encoded protein belongs to a family of NEDD4-like proteins, which are E3 ubiquitin-ligase molecules and regulate key trafficking decisions. The nucleotide sequence and amino acid sequence of human WWP1, is described in, for example, GenBank Accession No. gi:33946331. The nucleotide sequence and amino acid sequence of murine Wwp1, is described in, for example, GenBank Accession gi:112734835.

NFATc1 also referred to as NUCLEAR FACTOR OF ACTIVATED T CELLS, CYTOPLASMIC, CALCINEURIN-DEPENDENT 1 is a member of the NFAT family of transcription factors which regulates cytokine gene expression by binding to the promoter/enhancer regions of antigen-responsive genes, usually in cooperation with heterologous DNA-binding partners. The activation of NFAT proteins is controlled by calcineurin, the calmodulin-dependent phosphatase. Aramburu et al. (1998) identified a short conserved sequence in the NFATC1 protein (residues 107-119) that targets calcineurin to NFAT. There are 5 alternative transcripts of human NFATc1, the nucleotide sequence of which (and the amino acid sequences of the isoforms encoded thereby),are described in, for example, GenBank Accession No. gi:27502384, gi:27502385, gi:27502387, gi:27502390, and gi:27502392. There are 2 alternative transcripts of human NFATc1, the nucleotide sequence of which (and the amino acid sequences of the isoforms encoded thereby) are described in, for example, GenBank Accession No. gi:38348192 and gi:118131200.

"ATF4", also called "CREB2", and "Osterix", also called "SP7", are transcription factors belonging to the bZIP protein family and C2H2-type zinc-finger protein family, respectively, that are key regulators of bone matrix biosynthesis during remodeling of bone, e.g., during bone formation and mineralization (see, for example, Yang, X., et al. (2004). *Cell* 117, 387-398; Nakashima, K., et al. (2002). *Cell* 108, 17-2). BSP, ColI(α)1, ATF4, and Osterix are specific markers of bone formation and development. The nucleotide sequence and amino acid sequence of human ATF4, is described in, for example, GenBank Accession No. gi:33469975 and gi:33469973. The nucleotide sequence and amino acid sequence of murine ATF4, is described in, for example, GenBank Accession No. gi:6753127. The nucleotide sequence and amino acid sequence of human SP7, is described in, for example, GenBank Accession No. gi:22902135. The nucleotide sequence and amino acid sequence of murine SP7, is described in, for example, GenBank Accession No gi:18485517.

As used herein, the term "TAOK2", also referred to as "thousand-and-one amino acid kinase 2" or "TAO2 kinase" or "KIAA0881" or "MAP3K17" OR "PSK" OR "PSK-1" OR "PSK1" OR "TAO1" OR "TAO2" OR "hKFC—C" OR "Serine/threonine-protein kinase TAO2" OR "TAO kinase 2" OR "Thousand and one amino acid protein 2" OR "prostate derived STE20-like kinase PSK", refers to a serine/threonine protein kinase of the STE20 kinase family. See, for example, Huangfu W. C, et al. (2006) *J Biol Chem* 281(39):28802-10

The amino acid sequence of human TAOK2 is known and can be found in, for example, GenBank accession numbers GI:4759208 and GI:45505130. The nucleotide sequence of human TAOK2 can be found in, for example, GenBank accession number GI:4759208 and GI:45505130. The nucleotide and amino acid sequence of mouse TOAK2 may be found in, for example, GenBank accession number gi: 31324959.

As used herein, the term "DLG1" refers to a homologue of the *Drosophila* discs large tumor suppressor gene (hDlg), a member of the membrane-associated guanylate kinase family. See, for example, Yamamoto Y et al. (2004) *Oncogene* 23(22):3889-97.

The amino acid sequence of human DLG1 is known and can be found in, for example, GenBank accession numbers GI:4758162. The nucleotide sequence of human DLG1 can be found in, for example, GenBank accession number GI:4758162. The nucleotide and amino acid sequence of mouse DLG1 may be found in, for example, GenBank accession number GI:40254642

As used herein, the term "PIN1", also referred to as "Peptidyl-prolyl cis-trans isomerase NIMA-interacting 1" or "DOD" or "UBL5" or "dod" or "PPIase or "Peptidyl-prolyl cis-trans isomerase NIMA-interacting 1" or "Rotamase" or "peptidyl-prolyl cis/trans isomerase, NIMA-interacting" or "protein (peptidyl-prolyl cis/trans isomerase) NIMA-interacting 1", refers to an Peptidyl-prolyl cis-trans isomerase that regulates mitosis presumably by interacting with NIMA and attenuating its mitosis-promoting activity. See for example, Lu K P et al. (1996) *Nature* 380(6574):544-7.

The amino acid sequence of human PIN1 is known and can be found in, for example, GenBank accession numbers GI:5453898. The nucleotide and amino acid sequence of mouse PIN1 may be found in, for example, GenBank accession number GI:12963653.

As used herein, the term "LYK5", also referred to as "LYK5" or "FLJ90524" or "STRAD" or "STE20-related adapter protein" or "STRAD alpha" OR "Serologically defined breast cancer antigen NY-BR-96", refers to a pseudokinase which, in complex with CAB39, binds to and activates STK11. See for example, Baas A F et al. (2003) *EMBO J.* 22(12):3062-72.

The amino acid sequence of human LYK5 is known and can be found in, for example, GenBank accession numbers GI:51242960 or GI:51242955 or GI:51242957 or GI:31982873. The nucleotide sequence of human LYK5 can be found in, for example, GenBank accession number GI:51242960 or GI:51242955 or GI:51242957 or GI:31982873. The nucleotide and amino acid sequence of mouse LYK5 may be found in, for example, GenBank accession number GI:21312400.

As used herein, the term "MOBKL2C", also referred to as "MGC26743" or "MOB3C" or "MOB1, Mps One Binder kinase activator-like 2C" or "Mob1 homolog 2C" or "Mps one binder kinase activator-like 2C" or "Protein Mob3C", refers to a serine/threonine kinase of the MOB1/phocein family. See for example, Ota T et al. (2004) *Nat. Genet.* 36 (1), 40-45.

The amino acid sequence of human MOBKL2C is known and can be found in, for example, GenBank accession numbers GI:41406059 or GI:41406061. The nucleotide sequence of human MOBKL2C can be found in, for example, GenBank accession number GI:41406059 or GI:41406061. The nucleotide and amino acid sequence of mouse MOBKL2C may be found in, for example, GenBank accession number GI:30424984.

As used herein, the term "MAP4K2", also referred to as "BL44" OR "GCK" or "RAB8IP" or "B lymphocyte serine/threonine protein kinase" or "GC kinase" or "Germinal center kinase" or "MAPK/ERK kinase kinase kinase 2" or "MEK kinase kinase 2" or "MEKKK 2" or "Rab8 interacting protein" or "germinal centre kinase (GC kinase)" or "mitogen-activated protein kinase kinase kinase kinase 2" or "SLK", refers to a serine/threonine kinase of the STE20 family. See for example, Hao W et al. (2006) *J Biol Chem.* February 10; 281(6):3075-84.

The amino acid sequence of human MAP4K2 is known and can be found in, for example, GenBank accession number GI:22035600. The nucleotide sequence of human MAP4K2 can be found in, for example, GenBank accession number GI:22035600. The nucleotide and amino acid sequence of mouse MAP4K2 may be found in, for example, GenBank accession number GI:6678800

As used herein, the term "PACSIN2", also referred to as "OTTHUMP00000028650" or "SDPII" or "Protein kinase C and casein kinase substrate in neurons protein 2" or "syndapin II", refers to a cytoplasmic adaptor protein. See for example, Ritter B et al. (1999) *FEBS Lett.* 454(3):356-62.

The amino acid sequence of human PACSIN2 is known and can be found in, for example, GenBank accession number GI:6005826. The nucleotide sequence of human PACSIN2 can be found in, for example, GenBank accession number GI:6005826. The nucleotide and amino acid sequence of mouse PACSIN2 may be found in, for example, GenBank accession number GI:7106381.

As used herein, the term "DCAMKL1", also referred to as "DCLK" or "KIAA0369" or "Doublecortin-like and CAM kinase-like 1" or "doublecortin-like kinase", refers to a serine/threonine kinase of the calcium/calmodulin-dependent protein kinase family. See for example, Deuel T A et al. (2006) *Neuron* 49(1):41-53.

The amino acid sequence of human DCAMKL1 is known and can be found in, for example, GenBank accession number GI:4758128. The nucleotide sequence of human DCAMKL1 can be found in, for example, GenBank accession number GI:4758128. The nucleotide and amino acid sequence of mouse DCAMKL1 may be found in, for example, GenBank accession number GI:9910164.

As used herein, the term "DOCK4", also referred to as "FLJ34238" or "KIAA0716" or "MGC134911" or "MGC134912" or "Dedicator of cytokinesis protein 4" or "dedicator of cytokinesis 4", refers to a member of the CDM family of regulators of small GTPases. See for example, Yajnik V et al. (2003) *Cell.* 112(5):673-84.

The amino acid sequence of human DOCK4 is known and can be found in, for example, GenBank accession number GI:92091572. The nucleotide sequence of human DOCK4 can be found in, for example, GenBank accession number GI:92091572. The nucleotide and amino acid sequence of mouse DOCK4 may be found in, for example, GenBank accession number GI:62543571.

As used herein, the term "PARG1", also referred to as "RP11-255E17.1" or "ARHGAP29 protein" or "PTPL1-associated RhoGAP 1" or "Rho GTPase activating protein 29", refers to a member of the RhoGAP family of regulators of small GTPases. See for example, Myagmar B E et al. (2005) *Biochem Biophys Res Commun.* 329(3):1046-52.

The amino acid sequence of human PARG1 is known and can be found in, for example, GenBank accession number GI:38016932. The nucleotide sequence of human PARG1 can be found in, for example, GenBank accession number GI:38016932. The nucleotide and amino acid sequence of mouse PARG1 may be found in, for example, GenBank accession number GI:33563303.

As used herein, the term "TAOK3", also referred to as "thousand-and-one amino acid kinase 3" or "TAO3 kinase" or "DKFZp666H245" or "DPK" or "FLJ31808" or "JIK" or "KDS" or "MAP3K18" or "hKFC-A" or "CTCL tumor antigen HD-CL-09" or "Cutaneous T-cell lymphoma tumor antigen HD-CL-09" or "Dendritic cell-derived protein kinase" or "JNK/SAPK-inhibitory kinase" or "Jun kinase-inhibitory kinase" or "Kinase from chicken homolog A" or "Serine/threonine-protein kinase TAO3", refers to a serine/threonine protein kinase of the STE20 kinase family. See, for example, Yustein J T et al. (2003) *Oncogene* 22(40):6129-41.

The amino acid sequence of human TAOK3 is known and can be found in, for example, GenBank accession number GI:19923464. The nucleotide sequence of human TAOK3 can be found in, for example, GenBank accession number GI: 9923464. The nucleotide and amino acid sequence of mouse TOAK3 may be found in, for example, GenBank accession number gi:82899408.

As used herein, the term "TRPV6", also referred to as "ABP/ZF" or "CAT1" or "CATL" or "CaT1" or "ECAC2" or "HSA277909" or "LP6728" or "ZFAB" OR "Alu-binding protein with zinc finger domain" or "Calcium transport protein 1" or "Epithelial calcium channel 2" or "Transient receptor potential cation channel subfamily V member 6" or "calcium channel CaT1" or "epithelial apical membrane calcium transporter/channel CaT1", refers to a cation channel protein of the TRPV family. See, for example, Bodding M et al. (2005) *J Biol Chem.* 280(8): 7022-9.

The amino acid sequence of human TRPV6 is known and can be found in, for example, GenBank accession number GI:21.314682. The nucleotide sequence of human TRPV6 can be found in, for example, GenBank accession number GI: 21314682. The nucleotide and amino acid sequence of mouse TRPV6 may be found in, for example, GenBank accession number gi:28376639.

As used herein, the term "CLK1", also referred to as "CLK" or "CLK/STY" or "CDC-like kinase 1" or "CDC28/CDC2-like kinase", refers to a dual specificity protein kinase. See, for example, Menegay H J et al. (2000) *J Cell Sci.* 113 (Pt 18):3241-53.

The amino acid sequence of human CLK1 is known and can be found in, for example, GenBank accession number GI:67551263 or GI:67551261. The nucleotide sequence of human CLK1 can be found in, for example, GenBank accession number GI:67551263 or GI:67551261. The nucleotide and amino acid sequence of mouse CLK1 may be found in, for example, GenBank accession number gi:211038135.

As used herein, the term "AAK1", also referred to as "KIAA1048" or "MGC138170" or "AP2 associated kinase 1" or "Adaptor-associated kinase 1", refers to a member of Prk/Ark family of serine/threonine kinases, See, for example, Conner S D et al. (2002) *J Cell Biol.* 156(5):921-9.

The amino acid sequence of human AAK1 is known and can be found in, for example, GenBank accession number GI: 29570780. The nucleotide and amino acid sequence of mouse AAK1 may be found in, for example, GenBank accession number gi: 73695877.

As used herein, the term "PRKCA", also referred to as "AAG6" or "MGC129900" or "MGC129901" or "PKC-A" or "PKC-alpha" or "Protein kinase C alpha type" or "aging-associated gene 6", refers to an AGC family serine/threonine kinase, See, for example, Hsieh et al. (2006) *Biochem Biophys Res Commun.* 339(1):217-25

The amino acid sequence of human PRKCA is known and can be found in, for example, GenBank accession number GI: 4506067. The nucleotide and amino acid sequence of mouse PRKCA may be found in, for example, GenBank accession number gi: 6755078.

As used herein, the term "AKAP8", also referred to as "AKAP95" or "DKFZp586B1222" or "A kinase (PRKA) anchor protein 8" or "A kinase anchor protein 8" or "A-kinase anchor protein 95 kDa", refers to an protein kinase C binding-protein, See, for example, Arsenijevic T et al. (2006) *Cell Cycle.* 5(11):1217-22.

The amino acid sequence of human AKAP8 is known and can be found in, for example, GenBank accession number GI: 5031579. The nucleotide and amino acid sequence of mouse AKAP8 may be found in, for example, GenBank accession number gi: 31560394.

As used herein, the term "DGKI", also referred to "DGK-IOTA" or "Diacylglycerol kinase iota", refers to lipid kinase of the diacylglycerol kinase family. See, for example, Ding L et al. (1998) *J Biol Chem.* 273(49):32746-52.

The amino acid sequence of human DGKI is known and can be found in, for example, GenBank accession number GI: 4758156. The nucleotide sequence of human DGKI can be found in, for example, GenBank accession number GI: 4758156. The nucleotide and amino acid sequence of mouse DGKI may be found in, for example, GenBank accession number gi: 51711902.

As used herein, the term "SMARCB1", also referred to "BAF47" or "INI1" OR "RDT" or "SNF5" or "SNF5L15" or "Sfh1p" or "Snr1" or "Integrase interactor 1 protein" or "SWI/SNF related, matrix associated, actin dependent regulator of chromatin, subfamily b, member 1" or "malignant rhabdoid tumor suppressor" or "sucrose nonfermenting, yeast, homolog-like 1", refers to component of the hSWI/SNF global transcription activator complex. See, for example, Modena P et al. (2005) *Cancer Res.* 65(10):4012-9.

The amino acid sequence of human SMARCB1 is known and can be found in, for example, GenBank accession number GI: 55956801 or GI:27545326. The nucleotide sequence of human SMARCB1 can be found in, for example, GenBank accession number GI: 55956801 or GI:27545326. The nucleotide and amino acid sequence of mouse SMARCB1 may be found in, for example, GenBank accession number gi: 6755578.

As used herein, the term "CIB2", also referred "2810434123R1k" or "KIP2" or "Calcium and integrin-binding protein 2" or "DNA-dependent protein kinase catalytic subunit-interacting protein 2", refers to the CIB2 protein. See, for example, Seki N et al. (1999) *Biochim Biophys Acta.* 1444(1):143-7.

The amino acid sequence of human CIB2 is known and can be found in, for example, GenBank accession number GI:5453708. The nucleotide sequence of human CIB2 can be found in, for example, GenBank accession number GI:5453708. The nucleotide and amino acid sequence of mouse CIB2 may be found in, for example, GenBank accession number gi: 9790085.

As used herein, the term "STK33", also referred "Serine/threonine-protein kinase 33", refers to serine/threonine kinase 33. See, for example, Mujica A O et al (1999) *FEBS J* 272(19):4884-98.

The amino acid sequence of human STK33 is known and can be found in, for example, GenBank accession number GI: 23943882. The nucleotide sequence of human STK33 can be found in, for example, GenBank accession number GI: 23943882. The nucleotide and amino acid sequence of mouse STK33 may be found in, for example, GenBank accession number gi: 38087657.

As used herein, the term "STK39", also referred "DCHT" or "DKFZp686K05124" or "PASK" or "SPAK" or "STE20/SPS1-related proline-alanine-rich protein kinase" or "Ste-20-related kinase" or "small intestine SPAK-like kinase" or "Serine/threonine-protein kinase 39", refers to serine/threonine kinase 39. See, for example, Johnston A M et al. (2000) *Oncogene.* 19(37):4290-7.

The amino acid sequence of human STK39 is known and can be found in, for example, GenBank accession number GI: 115430252. The nucleotide sequence of human STK39 can be found in, for example, GenBank accession number GI: 115430252. The nucleotide and amino acid sequence of mouse STK39 may be found in, for example, GenBank accession number gi: 8394347.

As used herein, the term "NRGN", also referred "Neurogranin" or "Ng" or "RC3" or "hng" or "calmodulin-binding protein" or "protein kinase C substrate", refers to the protein kinase C substrate and calmodulin-binding protein, Neurogranin. See, for example, Zhabotinsky A M et al. (2006) *J Neurosci* 26(28):7337-47.

The amino acid sequence of human NRGN is known and can be found in, for example, GenBank accession number GI: 5453800. The nucleotide sequence of human NRGN can be found in, for example, GenBank accession number GI: 5453800. The nucleotide and amino acid sequence of mouse NRGN may be found in, for example, GenBank accession number gi: 11528516.

As used herein, the term "PIK3R1", also referred to as "GRB1" or "p85-ALPHA" or "PI3-kinase p85-subunit alpha" or "Phosphatidylinositol 3-kinase regulatory subunit alpha" or "PtdIns-3-kinase p85-alpha" or "phosphatidylinositol 3-kinase, regulatory, 1" or "phosphatidylinositol 3-kinase-associated p-85 alpha", refers to alpha regulatory subunit lipid kinase, phosphatidylinositol 3-kinase. See, for example, Terauchi Y et al. (2004) *Diabetes.* 53(9):2261-70.

The amino acid sequence of human PIK3R1 is known and can be found in, for example, GenBank accession number GI: 32455252 or GI:32455248 or GI:32455250. The nucleotide sequence of human PIK3R1 can be found in, for example, GenBank accession number GI: 32455252 or GI:32455248 or GI:32455250. The nucleotide and amino acid sequence of mouse PIK3R1 may be found in, for example, GenBank accession number gi: 117320524.

As used herein, the term "DLX-5", also referred to as "distal-less homeobox 5", refers to the homeobox protein, DLX-5, a known regulator of chondrocyte hypertrophy. See, for example, Hsu S H et al. (2006) *Mech Dev.* 123(11):819-30.

The amino acid sequence of human DLX-5 is known and can be found in, for example, GenBank accession number GI: 4885187. The nucleotide sequence of human DLX-5 can be found in, for example, GenBank accession number GI: 4885187. The nucleotide and amino acid sequence of mouse DLX-5 may be found in, for example, GenBank accession number gi: 38524596.

As used herein, the term "MSX-2", also referred to as "CRS2" or "FPP" or "HOX8" or "MSH" or "PFM" or "PFM1" or "Homeobox protein MSX-2" or "parietal foramina 1", refers to the homeobox protein, MSX-2, a known regulator of osteoblast differentiation. See, for example, Yoshizawa T et al. (2004) *Mol Cell Biol.* 24(8): 3460-72.

The amino acid sequence of human MSX-2 is known and can be found in, for example, GenBank accession number GI: 27886557. The nucleotide sequence of human MSX-2 can be found in, for example, GenBank accession number GI: 27886557. The nucleotide and amino acid sequence of mouse MSX-2 may be found in, for example, GenBank accession number gi: 7305283.

As used herein, the term "RANKL", also referred to as "TNFSF11" or "CD254" or "ODF" or "OPGL" or "TRANCE" or "Osteoclast differentiation factor" OR "Osteoprotegerin ligand" or "Receptor activator of nuclear factor kappa B ligand" or "TNF-related activation-induced cytokine" or "Tumor necrosis factor ligand superfamily member 11", refers to the osteoclast regulatory factor, tumor necrosis factor ligand superfamily member 11. See, for example, Collin-Osdoby P et al. (2004) *Circ Res.* 95(11): 1046-57.

The amino acid sequence of human RANKL is known and can be found in, for example, GenBank accession number GI:4507595 or GI:14790152. The nucleotide sequence of human RANKL can be found in, for example, GenBank accession number GI:4507595 or GI:14790152. The nucleotide and amino acid sequence of mouse RANKL may be found in, for example, GenBank accession number gi: 6755833.

As used herein, the term "MMP9", also referred to as "CLG4B" or "GELB" or "92 kDa gelatinase" or "92 kDa type IV collagenase" or "Gelatinase B" or "macrophage gelatinase" or "matrix metallopeptidase 9 (gelatinase B, 92 kDa gelatinase, 92 kDa type IV collagenase)" or "type V collagenase", refers to the matrix metallopeptidase 9 protein. MMP9 is commonly used as a marker of osteoclast differentiation. See, for example, Rolli M et al. (2003) *Proc Natl Acad Sci USA* 100(16):9482-7

The amino acid sequence of human MMP9 is known and can be found in, for example, GenBank accession number GI:74272287. The nucleotide sequence of human MMP9 can be found in, for example, GenBank accession number GI:74272287. The nucleotide and amino acid sequence of mouse MMP9 may be found in, for example, GenBank accession number gi: 7305277.

As used herein, the term "Cathepsin K" refers to the cysteine protease Cathepsin K, commonly used as a marker of osteoclast differentiation. See, for example, Sharma S M et al. (2007) *J Biol Chem.* 25; 282(21):15921-9. The nucleotide and amino acid sequence of human Cathepsin K may be found in, for example, GenBank accession number gi: 4503151. The nucleotide and amino acid sequence of mouse Cathepsin K may be found in, for example, GenBank accession number gi: 31982433.

As used herein, the term "calcitonin receptor", also referred to as "CALCR" or "CRT" or "CT-R" or "CTR" or "CTR1", refers to cell surface receptor for the hormone calcitonin. The calcitonin receptor is commonly used as a marker of osteoclast differentiation. See, for example, Kim M S et al. (2006) *J Biol Chem.* 281(2):1274-85. The nucleotide and amino acid sequence of human calcitonin receptor may be found in, for example, GenBank accession number gi: 4502547. The nucleotide and amino acid sequence of mouse calcitonin receptor may be found in, for example, GenBank accession number gi: 6680830.

As used herein, the term "B3-integrin", also referred to as "ITGB3" or "CD61", refers to the cell surface adhesion molecule, B3-integrin. B3-integrin is commonly used as a marker of osteoclast differentiation. The nucleotide and amino acid sequence of human B3-integrin may be found in, for example, GenBank accession number gi: 4502547. The nucleotide and amino acid sequence of mouse B3-integrin may be found in, for example, GenBank accession number GI:6680830.

As used herein, the term "TRAP", also referred to as "ACP5" or "MGC117378" or "Tr-ATPase" or "TR-AP" or "Tartrate-resistant acid ATPase" or "acidphosphatase 5, tartrate resistant" refers to tartrate resistant acid phosphatase. TRAP is commonly used as a marker of osteoclast differentiation. See, for example, Andersson G (1989) *Connect Tissue Res*. (1-4):151-8. The nucleotide and amino acid sequence of human TRAP may be found in, for example, GenBank accession number GI:4502547. The nucleotide and amino acid sequence of mouse TRAP may be found in, for example, GenBank accession number GI:6680624.

As used herein, the term "MAP3K11" (NCBI Gene ID: 4296)-, is also referred to as mitogen-activated protein kinase kinase kinase 11. Activation of this serine/threonine kinase (downstream of FGD1 and CDC42) appears to augment osteoblast differentiation and function through its ability to phosphorylate downstream targets that are essential in osteoblast biology, like Runx2 and/or ATF4. Reduction of endogenous MAP3K11 levels in human mesenchymal stem cells potently inhibits osteoblast lineage commitment in these cells. The nucleotide and amino acid sequence of human TRAP may be found in, for example, GenBank accession number gi:56237030. The nucleotide and amino acid sequence of mouse TRAP may be found in, for example, GenBank accession number gi:66392589.

As used herein, the term "WWP2" (NCBI Gene ID: 11060)—also referred to as WW domain containing E3 ubiquitin protein ligase 2, is a member of the NEDD4 Family of E3 Ubiquitin ligases, There are three alternative transcripts of human WWP2, the nucleotide sequence of which (and the amino acid sequences of the isoforms encoded thereby),are described in, for example, GenBank Accession No. gi:40806206, gi:40806208, and gi:40806210. The nucleotide and amino acid sequence of mouse Wwp2 may be found in, for example, GenBank accession number gi:31543965.

As used herein, the term "Smurf2" (NCBI Gene ID: 64750)—also referred to as SMAD specific E3 ubiquitin protein ligase 2, is a member of the NEDD4 Family of E3 Ubiquitin ligases. The nucleotide and amino acid sequence of human SMURF2 may be found in, for example, GenBank accession number gi:56550041. The nucleotide and amino acid sequence of mouse Smurf2 may be found in, for example, GenBank accession number gi:57977276.

As used herein, the term "RhoC"—(NCBI Gene ID: 11853)—also referred to a ras homolog gene family member C, is a small GTPase family member. There are three alternative transcripts of human RHOC, the nucleotide sequence of which (and the amino acid sequences of the isoforms encoded thereby),are described in, for example, GenBank Accession No. gi:111494247, gi:111494250, and gi:111494249. The nucleotide and amino acid sequence of mouse RhoC may be found in, for example, GenBank accession number gi:160415212.

As used herein, the term "Slc4A2"—(NCBI Gene ID: 24780)-, also referred to as solute carrier family 4, anion exchanger, member 2 (erythrocyte membrane protein band 3-like 1) is a chloride/bicarbonate anion exchange channel. The nucleotide sequence of human SLC4A2 can be found in, for example, GenBank accession number gi: 156071473. The nucleotide and amino acid sequence of mouse Slc4a2 may be found in, for example, GenBank accession number gi:161169000.

As used herein, the term "Plcb4"—(NCBI Gene ID: 18798)-, also referred to as phospholipase C, beta 4 is phospholipase C isoform. There are two alternative transcripts of human RHOC, the nucleotide sequence of which (and the amino acid sequences of the isoforms encoded thereby),are described in, for example, GenBank Accession No. gi:33469932 and gi:33469938. The nucleotide and amino acid sequence of mouse RhoC may be found in, for example, GenBank accession number gi:118130923.

As used herein, the term "Nhedc2"—(NCBI Gene ID: 97086)—also referred to as Na+/H+ exchanger domain containing 2, is a putative sodium/hydrogen exchange channel. The nucleotide sequence of human NHEDC2 can be found in, for example, GenBank accession number gi:47271478. The nucleotide and amino acid sequence of mouse NhedC2 may be found in, for example, GenBank accession number gi:142368598.

As used herein, the term "osteoblast regulator activity" includes the ability of an osteoblast regulator to modulate an activity associated with the formation of osteoblasts, e.g., the formation of mature osteoblasts, and/or the mineralization of bone. Exemplary osteoblast regulator activities include e.g., modulation of bone growth (osteoclastogenesis), modulation of bone mineralization, modulation of osteoclastogenesis, modulation of osteoblast versus osteoclast activity, e.g., in bone formation and/or remodeling of bone, modulation of the expression of BSP, ColI($\alpha$)1, OCN, RANKL, RSK2, RUNX2, Dlx-5, Msx-2, ALP, WWP1, and ATF4.

As used herein, the term "osteoclast regulator activity" includes the ability of an osteoclast regulator to modulate an activity associated with the formation of osteoclasts, e.g., the formation of mature osteoclasts. Exemplary osteoblast regulator activities include e.g., modulation of bone growth (osteoclastogenesis), modulation of bone mineralization, modulation of osteoclastogenesis, modulation of osteoblast versus osteoclast activity, e.g., in bone formation and/or remodeling of bone, modulation of the expression of NFATc1, TRAP, Cathepsin K, MMP9, $\beta$3-integrin, and Calcitonin receptor.

As used herein, the various forms of the term "modulate" are intended to include stimulation (e.g., increasing or upregulating a particular response or activity) and inhibition (e.g., decreasing or downregulating a particular response or activity).

In one embodiment, the osteoblast/osteoclast regulator activity is a direct activity, such as an association with an osteoblast/osteoclast regulator-target molecule or binding partner. As used herein, a "target molecule", "binding partner" or "osteoblast/osteoclast regulator binding partner" is a molecule with which an osteoblast/osteoclast regulator protein binds or interacts in nature, such that osteoblast/osteoclast regulator mediated function is achieved.

The term "interact" as used herein is meant to include detectable interactions between molecules, such as can be detected using, for example, a yeast two hybrid assay or coimmunoprecipitation. The term interact is also meant to include "binding" interactions between molecules. Interactions may be protein-protein or protein-nucleic acid in nature.

As used herein, the term "contacting" (i.e., contacting a cell e.g. a stem cell, with an compound) is intended to include incubating the compound and the cell together in vitro (e.g., adding the compound to cells in culture) or administering the compound to a subject such that the compound and cells of the subject are contacted in vivo. The term "contacting" is not intended to include exposure of cells to an osteoblast/osteoclast regulator modulator that may occur naturally in a subject (i.e., exposure that may occur as a result of a natural physiological process).

As used herein, the term "test compound" includes a compound that has not previously been identified as, or recognized to be, a modulator of osteoblast/osteoclast regulator activity and/or expression and/or a modulator of osteoblastogenesis, osteoclastogenesis, and/or a modulator of bone growth and/or mineralization.

The term "library of test compounds" is intended to refer to a panel or pool comprising a multiplicity of test compounds.

As used herein, the term "cell free composition" refers to an isolated composition which does not contain intact cells. Examples of cell free compositions include cell extracts and compositions containing isolated proteins.

As used herein, the term "indicator composition" refers to a composition that includes a protein of interest (e.g., an osteoblast/osteoclast regulator), for example, a cell that naturally expresses the protein, a cell that has been engineered to express the protein by introducing an expression vector encoding the protein into the cell, a cell that has been engineered to inhibit the expression of a regulator protein by introducing an expression vector comprising an shRNA molecule into the cell, or a cell free composition that contains the protein (e.g., purified naturally-occurring protein or recombinantly-engineered protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, a nucleic acid molecule of the invention is an siRNA molecule. In another embodiment, a nucleic acid molecule of the invention is an shRNA molecule. In one embodiment, a nucleic acid molecule of the invention mediates RNAi. In another embodiment, a nucleic acid molecule of the invention mediates translational inhibition. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999); Cottrell T R, and Doering T L. 2003. Trends Microbiol. 11:37-43; Bushman F. 2003. Mol Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described herein for use in antisense RNA can be employed in molecules that mediate RNAi.

As used herein, the term "nucleic acid" includes fragments or equivalents thereof (e.g., fragments or equivalents thereof an osteoblast regulator or an osteoclast regulator). The term "equivalent" is intended to include nucleotide sequences encoding functionally equivalent proteins, i.e., variant proteins which have the ability to bind to the natural binding partner(s) of the protein that retain their biological activity.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived.

As used herein, an "isolated protein" or "isolated polypeptide" refers to a protein or polypeptide that is substantially free of other proteins, polypeptides, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the protein is derived, or substantially free from chemical precursors or other chemicals when chemically synthesized. The language "substantially free of cellular material" includes preparations of protein in which the protein is separated from cellular components of the cells from which it is isolated or recombinantly produced.

The nucleic acids of the invention can be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes or nucleic acid molecules to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses, adeno-associated viruses, lentiviruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Preferably a host cell is a mammalian cell, e.g., a mouse cell, a human cell. In one embodiment, it is an epithelial cell. In another embodiment, a host cell is a mesenchymal stem cell. In yet another embodiment, a host cell is an osteoblast. In one embodiment, a host cell is a hematopoietic stem cell. In another embodiment, a host cell is an osteoclast.

As used herein, the term "transgenic cell" refers to a cell containing a transgene.

As used herein, a "transgenic animal" includes an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

As used herein, the term "antibody" is intended to include immunoglobulin molecules and immunologically active portions of immunoglobulin molecules, i.e., molecules that contain an antigen binding site which binds (immunoreacts with) an antigen, such as Fab and F(ab')$_2$ fragments, single chain antibodies, intracellular antibodies, scFv, Fd, or other fragments, as well as intracellular antibodies. Preferably, antibodies of the invention bind specifically or substantially specifically to osteoblast/osteoclast regulator molecules (i.e., have little to no cross reactivity with non-osteoblast/osteoclast regulator molecules). The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

As used herein, the term "disorders that would benefit from the modulation of osteoblast/osteoclast regulator expression and/or activity" includes disorders in which an osteoblast/osteoclast regulator activity is aberrant or which would benefit from modulation of an osteoblast/osteoclast regulator activity. Exemplary disorders include disorders, diseases, conditions or injuries in which modulation of bone formation and mineralization would be beneficial.

In one embodiment, small molecules can be used as test compounds. The term "small molecule" is a term of the art and includes molecules that are less than about 7500, less than about 5000, less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., Cane et al. 1998. Science 282:63), and natural product extract libraries. In another embodiment, the compounds are small, organic non-peptidic compounds. In a further embodiment, a small molecule is not biosynthetic. For example, a small molecule is preferably not itself the product of transcription or translation.

II. Screening Assays

The invention provides methods (also referred to herein as "screening assays") for identifying other modulators, i.e., candidate or test compounds or agents (e.g., peptidomimetics, small molecules or other drugs) which modulate regulator (osteoblast regulator and/or osteoclast regulator) activity and for testing or optimizing the activity of other agents.

For example, modulators of osteoblast/osteoclast regulator expression and/activity can be known (e.g., dominant negative inhibitors of TAOK2, DLG1, PIN1, LYK5, MOBKL2C, MAP4K2, PACSIN2, DCAMKL1, DOCK4, PARG1, TAOK3, TRPV6, CLK1, AAK1, PRKCA, AKAP8, DGKI, SMARCB1, CIB2, STK33, STK39, NRGN, PIK3R1, RASSF5, FRAP1, STK38, LATS1, LATS2, STK38L, GEFT, TNNI3K, STK4, RAF1, ARF1, C17orf31, EXO1, POT1, TERF2IP, MSH2, DKC1, MOBKL1A, MAP3K11, WWP2, SMURF2, GCK, WASF1, PPP2CB, PPP2R1A, CREBBP, CUL3, FBXW11, MELK, PLCL1, MAP3K3, DLGH1, NEK7, IRAK3, RHOC, SLC4A2, PLCB4, B-RAF, BMPR2, MAPK3, and NHEDC2 activity, osteoblast/osteoclast regulator antisense molecules, intracellular antibodies that interfere with osteoblast/osteoclast regulator activity, peptide inhibitors derived from osteoblast/osteoclast regulator) or can be identified using the methods described herein.

For example, in one embodiment, molecules which bind, e.g., to a regulator, or have a stimulatory or inhibitory effect on the expression and or activity of an osteoblast/osteoclast regulator can be identified.

In one embodiment, the ability of a compound to directly modulate the expression, and/or activity of a regulator is measured in an indicator composition using a screening assay of the invention.

In one embodiment, the indicator composition can be a cell that expresses the regulator protein, for example, a cell that naturally expresses or, more preferably, a cell that has been engineered to express the protein by introducing into the cell an expression vector encoding the protein. In one embodiment, the cell has been engineered to express and antisense osteoblast/osteoclast regulator. Preferably, the cell is a mammalian cell, e.g., a mouse cell and/or a human cell. In one embodiment, the cell is derived from an adult. In another embodiment, the cell is an osteoblast. In one embodiment, the osteoblast is a primary calvarial osteoblast. In another embodiment, the osteoblast is a C3H10T1/2 osteoblast. In another embodiment, the cell is a mature osteoblast. In another embodiment, the cell is a mesenchymal stem cell. In one embodiment, the cell is an osteoclast. In another embodiment, the cell is a hematopoietic stem cell. In one embodiment, a hematopoietic stem cell is CD11b$^{low/-}$ CD3$^-$ B220$^-$ c-fms$^+$. In one embodiment, a CD11b$^{low/-}$ CD3$^-$ B220$^-$ c-fms$^+$ cell is c-kit$^+$. In another embodiment, a CD11b$^{low/-}$ CD3$^-$ B220$^-$ c-fms$^+$ cell is c-kit$^-$.

In another embodiment, cells for use in the screening assays of the invention are primary cells, e.g., isolated cells cultured in vitro that have not been immortalized. In another embodiment, cells for use in the screening assays of the invention are immortalized cells, i.e., cells from a cell line. In one embodiment, the cell line is the MC3T3-E1 cell line. In another embodiment, the cell line is the 293T cell line. In yet another embodiment, the cell line is the RAW 264.7 cell line.

Alternatively, the indicator composition can be a cell-free composition that includes the protein (e.g., a cell extract or a composition that includes e.g., either purified natural or recombinant protein).

Compounds identified using the assays described herein can be useful for treating disorders associated with aberrant expression and/or activity of a regulator e.g., disorders that would benefit from modulation of osteoblastogenesis, modulation of bone mineralization, modulation of osteoclastogenesis, modulation of osteoblast versus osteoclast activity, e.g., in bone formation and/or remodeling of bone, modulation of the expression of BSP, ColI(α)1, OCN, Osterix, RANKL, ATF4, NFATc1, TRAP, Cathepsin K, MMP9, β3-integrin, and Calcitonin receptor, modulation of ATF4 protein levels, and/or modulation of the phosphorylation of ATF4.

Conditions that can benefit from modulation of an osteoblast/osteoclast regulator activity include diseases, disorders, conditions, or injuries in which modulation of bone formation and mineralization would be beneficial. In one embodiment, bone formation and mineralization is modulated in a postnatal subject. In another embodiment, bone formation and mineralization is modulated in an adult subject, e.g., a subject in which the epiphyseal discs of, for example, the long bones have disappeared, i.e., the epiphysis and the diaphysis have fused.

In another aspect, the invention pertains to a combination of two or more of the assays described herein. For example, a modulating agent can be identified using a cell-based or a cell-free assay, and the ability of the agent to modulate the activity of a regulator in vivo, e.g., in an animal, such as, for example, an animal model for, e.g., osteoporosis or osteopetrosis. In one embodiment, the animal model of osteoporosis is an animal model of bone loss in postmenopausal women, e.g., due to a decrease in estrogen and subsequent increase in FSH, e.g., a mouse model of osteoporosis, e.g., an ovariectomized mouse. In another embodiment, the animal model of osteoporosis is a model of secondary osteoporosis, e.g., glucocorticoid induced osteoporosis. In another embodiment, an animal model for use in the methods of the invention, e.g., a mouse model of osteopenia, is a transgenic mouse overexpressing WWP1. In one embodiment, the transgenic WWP1 mouse comprises a conditional allele of WWP1, e.g., an allele of WWP1 which spatially restricts the expression of WWP1 to, e.g., an osteoblast. In one embodiment, the conditional WWP1 allele comprises the human WWP1 allele. In one embodiment, WWP1 is expressed under the control of a tissue specific promoter. In one embodiment, a tissue specific promoter is a type I collagen promoter. In another embodiment, a tissue specific promoter is the Osterix promoter. In another embodiment, the animal model is a model of osteopetrosis is a knock-out mouse, e.g., a mouse with conditional ablation of NFATc1, e.g., Cre-lox NFATc1.

Moreover, a modulator of a regulator identified as described herein (e.g., an antisense nucleic acid molecule, or a specific antibody, or a small molecule) can be used in an animal model to determine the efficacy, toxicity, or side effects of treatment with such a modulator. Alternatively, a modulator identified as described herein can be used in an animal model to determine the mechanism of action of such a modulator.

In another embodiment, it will be understood that similar screening assays can be used to identify compounds that indirectly modulate the activity and/or expression of a regulator e.g., by performing screening assays such as those described above using molecules with which the regulator interacts, e.g., molecules that act either upstream or downstream of the regulator in a signal transduction pathway.

In one embodiment of the invention, the cell based and/or cell free assays are performed in a high-throughput manner. In one embodiment, the assays are performed using a 96-well format. In another embodiment, the assays of the invention are performed using a 192-well format. In another embodiment, the assays of the invention are performed using a 384-well format. In one embodiment, the assays of the invention are semi-automated, e.g., a portion of the assay is performed in an automated manner, e.g., the addition of various reagents. In another embodiment, the assays of the invention are fully automated, e.g., the addition of all reagents to the assay and the capture of assay results are automated.

The assays of the invention generally involve contacting an indicator composition with a compound of interest or a library of compounds for a predetermined amount of time or at a predetermined time of growth (either in vitro or in vivo) and assaying for the effect of the compound on a particular read-out. In one embodiment, an indicator composition is contacted with a compound of interest or a library of compounds for the duration of the assay. In another embodiment, an indicator composition is contacted with a compound of interest or a library of compounds for a period of time less than the entire assay time period. For example, cells may be cultured for a period of days or weeks and may be contacted with a compound following, for example, 14 days in culture. In one embodiment, cells are contacted with a compound of interest for 1, 2, 3, 4, 5, 6, 7, 8, 9, 10, 11, 12, 13, 14, 15, 16, 17, 18, 19, 20, or 21 days. In one embodiment, indicator compositions of the invention are contacted with a compound for a predetermined time period, the compound is removed, and the indicator composition is maintained in the absence of the compound for a predetermined period prior to assaying for a particular read-out. In addition, non-human animals for use in the methods of the invention (described in detail below) may be contacted with a compound of interest for 1, 2, 3, 4, 5, 6, 7, 8, 9, 10, 11, 12, 13, 14, 15, 16, 17, 18, 19, 20, 21 days, 4, 5, 6, 7, 8, 9, 10, 11, or 12 weeks. Non-human animals of the invention may also be, for example, ovariectomized or treated with glucocorticoids, and contacted with a compound of the invention, 0, 1 2, 3, 4, 5, 6, 7, 8, 9, 10, 11, or 12, weeks following surgery or treatment with a glucocorticoid. In another embodiment, non-human animals may be contacted with a compound of interest prior to surgery or treatment with a glucocorticoid, e.g., 1, 2, 3, 4, 5, 6, 7, 8, 9, 10, 11, 12, 13, 14 days prior to surgery or treatment.

The compounds of the invention may be assayed at concentrations suitable to the assay and readily determined by one of skill in the art. For example in one embodiment, indicator compositions are contacted with millimolar concentrations of compounds. In another embodiment, indicator compositions are contacted with micromolar concentrations of compounds. In another embodiment, indicator compositions are contacted with nanomolar concentrations of compounds.

The cell based and cell free assays of the invention are described in more detail below.

A. Cell Based Assays

The indicator compositions of the invention can be cells that express at least one of an osteoblast/osteoclast regulator protein, for example, a cell that naturally expresses the endogenous molecule or, more preferably, a cell that has been engineered to express at least one of an exogenous osteoblast/osteoclast regulator protein by introducing into the cell an expression vector encoding the protein(s). A cell for use in the methods of the invention may also be engineered by introducing into the cell an expression vector comprising a shRNA molecule that mediates RNAi of an osteoblast/osteoclast regulator. Alternatively, the indicator composition can be a cell-free composition that includes at least one of an osteoblast/osteoclast regulator (e.g., a cell extract from a cell expressing the protein or a composition that includes purified regulator protein, either natural or recombinant protein, or a cell extract from a cell expressing an osteoblast/osteoclast regulator shRNA molecule).

A variety of cell types are suitable for use as an indicator cell in the screening assay. In one embodiment, a cell line is used which expresses low levels of endogenous regulator and is then engineered to express recombinant protein. In another embodiment, a cell line is used which expresses high levels of endogenous osteoblast/osteoclast regulator and is then engineered to inhibit the production of the regulator protein. Cells for use in the subject assays include both eukaryotic and prokaryotic cells. For example, in one embodiment, a cell is a bacterial cell. In another embodiment, a cell is a fungal cell, such as a yeast cell. In another embodiment, a cell is a vertebrate cell, e.g., an avian cell or a mammalian cell (e.g., a murine cell, or a human cell). Preferably, the cell is a mammalian cell, e.g., a human cell. Alternatively, the indicator composition can be a cell-free composition that includes the protein (e.g., a cell extract or a composition that includes e.g., either purified natural or recombinant protein).

Compounds that modulate expression and/or activity of a regulator can be identified using various "read-outs."

For example, an indicator cell can be transfected with an expression vector, incubated in the presence and in the absence of a test compound, and the effect of the compound on the expression of the molecule or on a biological response regulated by the molecule can be determined. The biological activities of include activities determined in vivo, or in vitro, according to standard techniques. Activity can be a direct activity, such as an association with a target molecule or binding partner, or an enzymatic activity, such as a kinase activity, or a phosphatase activity. Alternatively, the activity is an indirect activity, such as a cellular signaling activity occurring downstream of the interaction of the protein with a target molecule or a biological effect occurring as a result of the signaling cascade triggered by that interaction. For example, biological activities of osteoblast/osteoclast regulators include: modulation of osteoblastogenesis, modulation of bone mineralization, modulation of osteoclastogenesis, modulation of osteoblast versus osteoclast activity, e.g., in bone formation and/or remodeling of bone, modulation of the expression of BSP, ColI($\alpha$)1, OCN, Osterix, RANKL, ATF4, NFATc1, TRAP, Cathepsin K, MMP9, $\beta$3-integrin, and Calcitonin receptor, modulation of ATF4 protein levels, and/or modulation of the phosphorylation of ATF4.

An indicator cell may also be transfected with an expression vector comprising an osteoblast/osteoclast regulator shRNA molecule incubated in the presence and in the absence of a test compound, the effect of the compound on a biological response regulated by the molecule can be determined and a compound that "rescues" or "reverses" the phenotype associated with silencing of the osteoblast/osteoclast regulator may be identified.

To determine whether a test compound modulates protein expression of an osteoblast/osteoclast regulator, in vitro transcriptional assays can be performed. In one example of such an assay, a regulatory sequence (e.g., the full length promoter and enhancer) of an osteoblast/osteoclast regulator can be operably linked to a reporter gene such as chloramphenicol acetyltransferase (CAT), GFP, or luciferase, e.g., OSE2-luciferase, and introduced into host cells. In one embodiment, a reporter gene construct is a multimerized construct. In one embodiment, the multimerized construct comprises the osteocalcin regulatory sequence. In one embodiment, the multimerized osteocalcin construct comprises six copies of the osteocalcin regulatory sequence operably linked to a luciferase reporter gene. Other techniques are known in the art.

To determine whether a test compound modulates mRNA expression of an osteoblast/osteoclast regulator, or the expression of genes modulated by an osteoblast/osteoclast regulator, e.g., BSP, ColI($\alpha$)1, OCN, RANKL, ATF4, NFATc1, TRAP, Cathepsin K, MMP9, $\beta$3-integrin, and Calcitonin receptor, various methodologies readily known to one of skill in the art can be performed, such as quantitative or real-time PCR.

To determine whether a test compound modulates the activity of a regulator, assays of the known function of the regulator may be performed using methods known to one of skill in the art.

As used interchangeably herein, the terms "operably linked" and "operatively linked" are intended to mean that the nucleotide sequence is linked to a regulatory sequence in a manner which allows expression of the nucleotide sequence in a host cell (or by a cell extract). Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

A variety of reporter genes are known in the art and are suitable for use in the screening assays of the invention. Examples of suitable reporter genes include those which encode chloramphenicol acetyltransferase, beta-galactosidase, alkaline phosphatase, green fluorescent protein, or luciferase. Standard methods for measuring the activity of these gene products are known in the art.

In one embodiment, the level of expression and/or activity of an osteoblast/osteoclast regulator or of the reporter gene in the indicator cell in the presence of the test compound is higher than the level of expression and/or activity in the indicator cell in the absence of the test compound and the test compound is identified as a compound that stimulates the expression of an osteoblast/osteoclast regulator. In another embodiment, the level of expression and/or activity of an osteoblast/osteoclast regulator or of the reporter gene in the indicator cell in the presence of the test compound is lower than the level of expression and/or activity in the indicator cell in the absence of the test compound and the test compound is identified as a compound that inhibits the expression of an osteoblast/osteoclast regulator.

In one embodiment, the invention provides methods for identifying compounds that modulate cellular responses in which an osteoblast/osteoclast regulator is involved.

In one embodiment differentiation of cells, e.g., mesenchymal and/or hematopoietic stem cells, can be used as an indicator of modulation of an osteoblast/osteoclast regulator. Cell differentiation can be monitored directly (e.g. by microscopic examination of the cells for monitoring cell differentiation), or indirectly, e.g., by monitoring one or more markers of cell differentiation (e.g., an increase in mRNA for a gene product associated with cell differentiation, or the secretion of a gene product associated with cell differentiation, such as the secretion of a protein (e.g., TRAP) or the expression of a marker of osteoblast and/or osteoclast development as described herein. Standard methods for detecting mRNA of interest, such as reverse transcription-polymerase chain reaction (RT-PCR) and Northern blotting, are known in the art. Standard methods for detecting protein secretion in culture supernatants, such as enzyme linked immunosorbent assays (ELISA), are also known in the art. Proteins can also be detected using antibodies, e.g., in an immunoprecipitation reaction or for staining and FACS analysis.

In one embodiment, the ability of the compound to modulate bone formation and mineralization and/or osteoclastogenesis can be measured. Various in vitro techniques for determining the ability of compound to modulate bone formation and mineralization and/or osteoclastogenesis are known to the skilled artisan. For example, skeletal architecture can be assayed by digital radiography of, trabeculation (i.e., the anastomosing bony spicules in cancerous bone which form a meshwork of intercommunicating spaces that are filled with bone marrow) can be determined by three-dimensional μ-QCT imaging, and by analyses of bone cross-sections. In addition, trabecular number, trabecular thickness, trabecular spacing, bone volume per tissue volume (BV/TV), and bone mineral density (BMD) can also be determined by μ-QCT imaging. These analyses can be performed on whole skeleton preparations or individual bones. Mineralized bone and non-mineralized cartilage formation can be determined by histochemical analyses, such as by alizarin red/alcian blue staining. To assay a compound for an effect on osteoblast function versus osteoclast function and/or osteoclastogenesis, in vitro osteoclast differentiation assays are performed by culturing bone marrow (BM) (hematopoietic stem cells) in the presence of M-CSF and RANKL to generate TRAP+ osteoclasts. TRAP secretion by osteoclasts can be determined using a colorimetric assay. In vivo determinations of whether a compound effects osteoblast function or osteoclast can be performed by, for example, bone marrow transfers. In addition, various histomorphometric parameters can be analyzed to determine bone formation rates. For example, dual calcein-labeling of bone visualized with fluorescent micrography allows the determination of bone formation rate (BFR), which is calculated by multiplying the mineral apposition rate (MAR), which is a reflection of the bone formation capabilities of osteoblasts, by the area of mineralized surface per bone surface (MS/BS). In one embodiment, a chelating fluorochrome, e.g., xylenol orange can be used to visualize bone. In addition, the total osteoblast surface, which a reliable indicator of osteoblast population, can be measured, as can osteoid thickness, i.e., the thickness of bone that has not undergone calcification. Sections of bone can also be analyzed by staining with Von Kossa and Toluidine Blue for analysis of in vivo bone formation and serum levels of, for example, Trabp5b and deoxypyridinoline can be determined as an indication of bone formation. The ex vivo culturing of osteoblast precursors and immature osteoblasts can also be performed to determine if cells possess the capacity to form mineralized nodules, which reflects the generation of extracellular matrix, i.e., the mineralized matrix of bone. Furthermore, these cultures can be assayed for their proliferative ability, e.g., by cell counting, and can be stained for the presence of various markers of bone formation, such as for example, alkaline phosphatase. These same cultures can also be used for various analyses of mRNA and protein production of numerous molecules known to be involved in bone formation and mineralization, and osteoclastogenesis, such as, for example, BSP, ColI(α)1, OCN, Osterix, RANKL, ATF4, NFATc1, TRAP, Cathepsin K, MMP9, β3-integrin, Calcitonin receptor, ALP, LRP5, Runx2, RANKL, RSK2.

The ability of a compound to modulate bone formation and mineralization can also be measured using cultured cells. In one embodiment, a mesenchymal stem cell may be used in an assay for bone formation. For example, a pluripotent cell capable to forming an osteoblast, i.e., mesenchymal stem cells (e.g., a primary cell or a cell line, can be contacted with a compound of interest and the differentiation of the pluripotent cell into an osteoblast can be visually assessed. The differentiation of the pluripotent cell into an osteoblast can also be assessed by assaying the level of cellular alkaline phosphatase using a colorimetric assay. In one embodiment, total cell number is normalized to the level of cellular alkaline phosphatase by staining the cells with, for example, Alamar blue. The mineralization of such cultured, differentiated cells can be determined by, for example xylenol orange staining and/or von Kossa staining.human) may be plated for culture on day 0. On day 1, cells may be differentiated. Also on day 1, test compounds may be added to the cultures. Differentiation may be analyzed (e.g., on day 4-10) using an alkaline phosphatase assay and cell viability may be measured using alamar blue. Extracellular matrix formation may also be measured, e.g., on day 21.

In another embodiment, a hematopoietic stem cell may be used in an assay for bone formation. For example, a pluripotent cell capable to forming an osteoclast, i.e., hematopoietic stem cells (e.g., a primary cell or a cell line, can be contacted with a compound of interest and the differentiation of the pluripotent cell into an osteoclast can be visually assessed. The differentiation of the pluripotent cell into an osteoclast can also be assessed by assaying the level of TRAP secreted into the culture medium using a colorimetric assay. In one embodiment, total cell number is normalized to the level of TRAP by staining the cells with, for example, Alamar blue. The formation of osteoclasts or resorption lacunae can be assessed by, for example von Kossa staining.

In another embodiment, the ability of a compound to modulate apoptosis can be determined. In one embodiment, cytochrome C release from mitochondria during cell apoptosis can be detected, e.g., plasma cell apoptosis (as described in, for example, Bossy-Wetzel E. et al. (2000) *Methods in Enzymol.* 322:235-42). Other exemplary assays include: cytofluorometric quantization of nuclear apoptosis induced in a cell-free system (as described in, for example, Lorenzo H. K. et al. (2000) *Methods in Enzymol.* 322:198-201); apoptotic nuclease assays (as described in, for example, Hughes F. M. (2000) *Methods in Enzymol.* 322:47-62); analysis of apoptotic cells, e.g., apoptotic plasma cells, by flow and laser scanning cytometry (as described in, for example, Darzynkiewicz Z. et al. (2000) *Methods in Enzymol.* 322:18-39); detection of apoptosis by annexin V labeling (as described in, for example, Bossy-Wetzel E. et al. (2000) *Methods in Enzymol.* 322:15-18); transient transfection assays for cell death genes (as described in, for example, Miura M. et al: (2000) *Methods in Enzymol.* 322:480-92); and assays that detect DNA cleavage in apoptotic cells, e.g., apoptotic plasma cells (as described in, for example, Kauffman S. H. et al. (2000) *Methods in Enzymol.* 322:3-15). Apoptosis can also be measured by propidium iodide staining or by TUNEL assay.

In another embodiment, intracellular calcium mobilization, protein levels of members of the NFAT cascade can be measured.

In another embodiment, the effect of the compound on ubiquitination of, for example, RSK2, and/or Runx2, can be measured, by, for example in vitro or in vivo ubiquitination assays. In vitro ubiquitination assays are described in, for example, Fuchs, S. Y., B et al. (1997) *J. Biol. Chem.* 272: 32163-32168. In vivo ubiquitination assays are described in, for example, Treier, M., L. et al. (1994) *Cell* 78:787-798.

In one embodiment, a low throughput assay may be used to assess the effect of a compound on ubiquitination. In another embodiment, a high throughput assay may be used to screen for compounds that affect ubiquitination. For example, an antibody recognizing a protein tag (e.g., myc) may be bound to the wells of a plate. Epitope-tagged WWP1 comprising a HECT domain may then be bound to the antibody on the plate.

In another embodiment, the effect of the compound on the degradation of, for example, an endogenous osteoblast/osteoclast regulator target molecule and/or an osteoblast/osteoclast regulator binding partner, can be measured by, for example, coimmunoprecipitation. Western blotting of the coimmunoprecipitate and probing of the blots with antibodies to the osteoblast/osteoclast regulator and the endogenous osteoblast/osteoclast regulator target molecule and/or the osteoblast/osteoclast regulator binding partner can be quantitated to determine whether degradation has occurred. Pulse-chase experiments can also be performed to determine protein levels.

In another embodiment, the phosphorylation of an osteoblast/osteoclast regulator is determined. Phosphorylation can be determined by, for example, the use of in vitro kinase assays, and the autophosphorylation of a protein, can be measured by, for example, immunoblotting with antibodies specific for phosphorylated and/or unphosphorylated forms of the protein, and/or immunoblotting with an antibody that recognizes phosphorylated serine/threonine.

The ability of the test compound to modulate binding of an osteoblast/osteoclast regulator to a substrate or target molecule can also be determined. Determining the ability of the test compound to modulate binding of an an osteoblast/osteoclast regulator to a target molecule (e.g., a binding partner such as a substrate) can be accomplished, for example, by coupling the target molecule with a radioisotope or enzymatic label such that binding of the target molecule to the osteoblast/osteoclast regulator can be determined by detecting the labeled target molecule in a complex. Alternatively, an osteoblast/osteoclast regulator be coupled with a radioisotope or enzymatic label to monitor the ability of a test compound to modulate binding to a target molecule in a complex. Determining the ability of the test compound to bind to an osteoblast/osteoclast regulator can be accomplished, for example, by coupling the compound with a radioisotope or enzymatic label such that binding of the compound to the osteoblast/osteoclast regulator can be determined by detecting the labeled compound in a complex. For example, targets can be labeled with $^{125}$I, $^{35}$S, $^{14}$C, or $^{3}$H, either directly or indirectly, and the radioisotope detected by direct counting of radioemmission or by scintillation counting. Alternatively, compounds can be labeled, e.g., with, for example, horseradish peroxidase, alkaline phosphatase, or luciferase, and the enzymatic label detected by determination of conversion of an appropriate substrate to product.

It is also within the scope of this invention to determine the ability of a compound to interact with an osteoblast/osteoclast regulator without the labeling of any of the interactants. For example, a microphysiometer can be used to detect the interaction of a compound with an osteoblast/osteoclast regulator molecule without the labeling of either the compound or the molecule (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and The cells of the invention can express at least one of an osteoblast/osteoclast regulator, may be engineered to do so, or may be engineered to silence the production of the protein using recombinant technology. For example, a cell that has been engineered to express the protein can be produced by introducing into the cell an expression vector encoding the protein.

Recombinant expression vectors that can be used for expression of an osteoblast/osteoclast regulator are known in the art. For example, the cDNA or shRNA molecule is first introduced into a recombinant expression vector using standard molecular biology techniques. A cDNA can be obtained, for example, by amplification using the polymerase chain reaction (PCR) or by screening an appropriate cDNA library. The nucleotide sequences of cDNAs for or a molecule in a signal transduction pathway involving (e.g., human, murine and yeast) are known in the art and can be used for the design of PCR primers that allow for amplification of a cDNA by standard PCR methods or for the design of a hybridization probe that can be used to screen a cDNA library using standard hybridization methods. Similarly a shRNA molecule can be designed based on the known coding sequence of an osteoblast/osteoclast regulator as disclosed herein.

Following isolation or amplification of a cDNA molecule encoding an osteoblast/osteoclast regulator the DNA fragment is introduced into an expression vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors and/or viral vectors, e.g., lentiviruses) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses, adeno-associated viruses, and lentiviruses), which serve equivalent functions.

The recombinant expression vectors of the invention comprise a nucleic acid molecule in a form suitable for expression of the nucleic acid in a host cell, which means that the recombinant expression vectors include one or more regulatory sequences, selected on the basis of the host cells to be used for expression and the level of expression desired, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell, those which direct expression of the nucleotide sequence only in certain host cells (e.g., tissue-specific regulatory sequences) or those which direct expression of the nucleotide sequence only under certain conditions (e.g., inducible regulatory sequences).

When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDM8 (Seed, B., (1987) *Nature* 329:840) and pMT2PC (Kaufman et al. (1987), *EMBO J.* 6:187-195). A variety of mammalian expression vectors carrying different regulatory sequences are commercially available. For constitutive expression of the nucleic acid in a mammalian host cell, a preferred regulatory element is the cytomegalovirus promoter/enhancer and/or a U6 promoter. Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nuc. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Still further, many tissue-specific regulatory sequences are known in the art, including the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916) and mammary gland-specific promoters (e.g., milk whey promoter; U.S. Pat. No. 4,873,316 and European Application Publication No. 264,166), the type I collagen promoter or the Osterix promoter to direct expression in osteoblasts.). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Vector DNA can be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook et al. (*Molecular Cloning: A Laboratory Manual*, 2nd Edition, Cold Spring Harbor Laboratory press (1989)), and other laboratory manuals. Vector DNA can also be introduced into mammalian cells by infection with, for example, a viral vector, e.g., one incorporated into a viral particle.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on a separate vector from that encoding an osteoblast/osteoclast regulator or, more preferably, on the same vector. Cells stably transfected with the introduced nucleic acid can be identified by drug selection (e.g., cells that have incorporated the selectable marker gene will survive, while the other cells die).

In one embodiment, within the expression vector coding sequences are operatively linked to regulatory sequences that allow for constitutive expression of the molecule in the indicator cell (e.g., viral regulatory sequences, such as a cytomegalovirus promoter/enhancer, can be used). Use of a recombinant expression vector that allows for constitutive expression of an osteoblast/osteoclast regulator in the indicator cell is preferred for identification of compounds that enhance or inhibit the activity of the molecule. In an alternative embodiment, within the expression vector the coding sequences are operatively linked to regulatory sequences of the endogenous gene for the osteoblast/osteoclast regulator (i.e., the promoter regulatory region derived from the endogenous gene). Use of a recombinant expression vector in which expression is controlled by the endogenous regulatory sequences is preferred for identification of compounds that enhance or inhibit the transcriptional expression of the molecule.

In yet another aspect of the invention, the osteoblast/osteoclast regulator protein or fragments thereof, can be used as "bait protein" e.g., in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268: 12046-12054; Bartel et al. (1993) *Biotechniques* 14:920-924; Iwabuchi et al. (1993) *Oncogene* 8:1693-1696; and Brent WO94/10300), to identify other proteins, which bind to or interact with the osteoblast/osteoclast regulator ("binding proteins" or "bp") and are involved in osteoblast/osteoclast regulator activity. Such binding proteins are also likely to be involved in the propagation of signals by the osteoblast/osteoclast regulator proteins or osteoblast/osteoclast regulator targets such as, for example, downstream elements of an osteoblast/osteoclast regulator-mediated signaling pathway. Alternatively, such binding proteins can be osteoblast/osteoclast regulator inhibitors.

The two-hybrid system is based on the modular nature of most transcription factors, which consist of separable DNA-binding and activation domains. Briefly, the assay utilizes two different DNA constructs. In one construct, the gene that codes for an osteoblast/osteoclast regulator protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an osteoblast/osteoclast regulator dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the osteoblast/osteoclast regulator protein.

B. Cell-Free Assays

In another embodiment, the indicator composition is a cell free composition. At least one of an osteoblast/osteoclast regulator expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies can be used to produce a purified or semi-purified protein that can be used in a cell free composition. Alternatively, a lysate or an extract of cells expressing the protein of interest can be prepared for use as cell-free composition.

In one embodiment, compounds that specifically modulate an osteoblast/osteoclast regulator activity are identified based on their ability to modulate the interaction of an osteoblast/osteoclast regulator with a target molecule to which the osteoblast/osteoclast regulator binds. The target molecule can be a DNA molecule, e.g., an osteoblast/osteoclast regulator-responsive element or a protein molecule. Suitable assays are known in the art that allow for the detection of protein-protein interactions (e.g., immunoprecipitations, two-hybrid assays and the like) or that allow for the detection of interactions between a DNA binding protein with a target DNA sequence (e.g., electrophoretic mobility shift assays, DNAse I footprinting assays, oligonucleotide pull-down assays, and the like). By performing such assays in the presence and absence of test compounds, these assays can be used to identify compounds that modulate (e.g., inhibit or enhance) the interaction of an osteoblast/osteoclast regulator with a target molecule.

In one embodiment, the amount of binding of an osteoblast/osteoclast regulator to the target molecule in the presence of the test compound is greater than the amount of binding of an osteoblast/osteoclast regulator to the target molecule in the absence of the test compound, in which case the test compound is identified as a compound that enhances binding of the osteoblast/osteoclast regulator to a target. In another embodiment, the amount of binding of the osteoblast/osteoclast regulator to the target molecule in the presence of the test compound is less than the amount of binding of the osteoblast/osteoclast regulator to the target molecule in the absence of the test compound, in which case the test compound is identified as a compound that inhibits binding of the osteoblast/osteoclast regulator to the target. Binding of the test compound to an osteoblast/osteoclast regulator can be determined either directly or indirectly as described above. Determining the ability of an osteoblast/osteoclast regulator protein to bind to a test compound can also be accomplished using a technology such as real-time Biomolecular Interaction Analysis (BIA) (Sjolander, S, and Urbaniczky, C. (1991) *Anal. Chem.* 63:2338-2345; Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In the methods of the invention for identifying test compounds that modulate an interaction between an osteoblast/osteoclast regulator and a target molecule, a polypeptide comprising the complete amino acid sequence of the osteoblast/osteoclast regulator can be used in the method, or, alternatively, a polypeptide comprising only portions of the protein can be used. An assay as described herein can be used to identify test compounds that either stimulate or inhibit the interaction between the osteoblast/osteoclast regulator protein and a target molecule. A test compound that stimulates the interaction between the protein and a target molecule is identified based upon its ability to increase the degree of interaction between, e.g., an osteoblast/osteoclast regulator and a target molecule as compared to the degree of interaction in the absence of the test compound. A test compound that inhibits the interaction between the protein and a target molecule is identified based upon its ability to decrease the degree of interaction between the protein and a target molecule as compared to the degree of interaction in the absence of the compound.

In one embodiment of the above assay methods of the present invention, it may be desirable to immobilize either an osteoblast/osteoclast regulator or a respective target molecule for example, to facilitate separation of complexed from uncomplexed forms of one or both of the proteins, or to accommodate automation of the assay. Binding of a test compound to an osteoblast/osteoclast regulator or interaction of an osteoblast/osteoclast regulator protein with a target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided in which a domain that allows one or both of the proteins to be bound to a matrix is added to one or more of the molecules. For example, glutathione-S-transferase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or osteoblast/osteoclast regulator protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either an osteoblast/osteoclast regulator protein or a target molecule can be immobilized utilizing conjugation of biotin and streptavidin. Biotinylated protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical), for example.). Alternatively, antibodies which are reactive with protein or target molecules but which do not interfere with binding of the protein to its target molecule can be derivatized to the wells of the plate, and unbound target or osteoblast/osteoclast regulator protein is trapped in the wells by antibody conjugation. Methods for detecting such complexes, in addition to those described above for the GST-immobilized complexes, include immunodetection of complexes using antibodies reactive with osteoblast/osteoclast regulator or target molecule, as well as enzyme-linked assays which rely on detecting an enzymatic activity associated with the osteoblast/osteoclast regulator protein or target molecule.

C. In Vivo Assays

In one embodiment, an in vivo assay may be used to analyze the ability of a compound to modulate bone formation and mineralization and/or osteoclastogenesis. For example, in one embodiment, a test compound is administered to mice and the effect of the compound on bone formation in the mice is measured using techniques that are known in the art. For example, sections of bone can also be analyzed by staining with Von Kossa and Toluidine Blue for analysis of in vivo bone formation. In one embodiment, levels of osteoclacin, TRAP 5b and/or deoxypyridinoline (DPD), e.g., in serum or other body fluids may be measured using techniques known in the art.

In one embodiment, the mice are postnatal mice. In one embodiment the mice are adult mice and the effect of the compound on adult bone formation is tested. In another embodiment, the mice are female mice. In another embodiment, the mice are ovariectomized mice. In another embodiment, the mice have been treated with glucocorticoids.

In yet another embodiment, the mice are transgenic mice overexpressing WWP1. In another embodiment, the mice express a conditional allele of WWP1. In yet another embodiment, the conditional allele restricts WWP1 expression to osteoblast cells (e.g., a type I collagen promoter or an Osterix promoter).

In another embodiment, the mice have a conditionally ablated NFATc1 gene.

In another embodiment, the ability of a compound to modulate bone formation in a tumor metastasis model is tested. For example, in one embodiment, tumor cells (e.g., human tumor cells such as breast cancer cells) are injected into immunodeficient mice (e.g., by intracardiac or intratibial injection) and the ability of the compound to affect bone formation in the animals is determined.

In another embodiment, the invention provides methods for identifying compounds that modulate a biological effect of an osteoblast/osteoclast regulator using cells deficient in at least one of an osteoblast/osteoclast regulator. Specific cell types, e.g., lymphoid cells (e.g., thymic, splenic and/or lymph node cells) or purified cells such as T cells, B cells, osteoblasts, osteoclasts, stem cells, from such animals can be used in screening assays.

Similarly, the invention provides methods for identifying compounds that modulate a biological effect of an osteoblast/osteoclast regulator using cells overexpressing WWP1. Cells overexpressing WWP1 can be used to identify agents that modulate a biological response regulated by an osteoblast/osteoclast regulator by modulating the biological activity of WWP1 (i.e., compounds that "rescue" the osteogenic phenotype of WWP1 overexpression). In one embodiment, a "conditional knock-out" system, in which the gene is overproduced in a spatially restricted manner, can be used to create transgenic cells for use in the screening assays. For example, a WWP1 gene can be operably linked to a type I collagen promoter or the osterix promoter and this construct can be used to create cells, or animals from which cells can be isolated, that overexpress WWP1 in a controlled manner and spatially restricts the expression of WWP1. Specific cell types, e.g., osteoblasts or purified cells such as mesenchymal stem cells, osteoblasts, osteoclasts, hematopoietic stem cells from such animals can be used in screening assays.

In another embodiment, invention provides methods for identifying compounds that modulate a biological effect of an osteoblast/osteoclast regulator using NFATc1 knock-out cells. NFATc1 knock-out cells can be used to identify agents that modulate a biological response regulated by an osteoblast/osteoclast regulator by modulating the biological activity of NFATc1 (i.e., compounds that "rescue" the osteopetrotic phenotype of NFATc1 ablation). In one embodiment, a "conditional knock-out" system, in which the gene is deleted in a temporally restricted manner, can be used to create cells for use in the screening assays. Specific cell types, e.g., osteoblasts or purified cells such as mesenchymal stem cells, osteoblasts, osteoclasts, hematopoietic stem cells from such animals can be used in screening assays.

In the screening methods, cells deficient in at least one of an osteoblast/osteoclast regulator or NFATc1 knock-out cells or transgenic WWP1 cells (hereinafter, collectively referred to as transgenic cells for simplicity) can be contacted with a test compound and a biological response regulated by the osteoblast/osteoclast regulator can be monitored. Modulation of the response in transgenic cells (as compared to an appropriate control such as, for example, untreated cells or cells treated with a control agent or appropriate wild-type cells) identifies a test compound as a modulator of the osteoblast/osteoclast regulator regulated response.

In one embodiment, the test compound is administered directly to a non-human transgenic animal, preferably a mouse (e.g., a mouse in which an osteoblast/osteoclast regulator gene is conditionally disrupted by means described above, or a chimeric mouse in which the lymphoid organs are deficient in osteoblast/osteoclast regulator, or an NFATc1 knockout mouse (as described above), or a WWP1 transgenic mouse overexpressing WWP1 as described above) to identify a test compound that modulates the in vivo responses of such transgenic cells. In another embodiment, transgenic cells are isolated from the non-human animals of the invention and contacted with the test compound ex vivo to identify a test compound that modulates a response regulated by an osteoblast/osteoclast regulator in the cells.

Transgenic cells can be obtained from a non-human animals created to be deficient in an osteoblast/osteoclast regulator, or NFATc1 knockout animals, or animals in which the WWP1 gene is overexpressed. Preferred non-human animals include monkeys, dogs, cats, mice, rats, cows, horses, goats and sheep. In preferred embodiments, the deficient animal is a mouse. Mice deficient in an osteoblast/osteoclast regulator or NFATc1 (or overexpressing WWP1) can be made using methods known in the art. Non-human animals deficient in a particular gene product typically are created by homologous recombination. In an exemplary embodiment, a vector is prepared which contains at least a portion of the gene into which a deletion, addition or substitution has been introduced to thereby alter, e.g., functionally disrupt, the endogenous gene. The gene preferably is a mouse gene. For example, a mouse osteoblast/osteoclast regulator gene can be isolated from a mouse genomic DNA library using the mouse osteoblast/osteoclast regulator cDNA as a probe. The mouse gene then can be used to construct a homologous recombination vector suitable for modulating an endogenous osteoblast/osteoclast regulator gene in the mouse genome. In a preferred embodiment, the vector is designed such that, upon homologous recombination, the endogenous gene is functionally disrupted (i.e., no longer encodes a functional protein; also referred to as a "knock out" vector).

Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced gene has homologously recombined with the endogenous gene are selected (see e.g., Li, E. et al. (1992) Cell 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In one embodiment of the screening assay, compounds tested for their ability to modulate a biological response regulated by, for example, an osteoblast/osteoclast regulator are contacted with transgenic cells by administering the test compound to a non-human animal in vivo and evaluating the effect of the test compound on the response in the animal.

The test compound can be administered to an animal as a pharmaceutical composition. Such compositions typically comprise the test compound and a pharmaceutically acceptable carrier. As used herein the term "pharmaceutically acceptable carrier" includes any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Except insofar as any conventional media or compound is incompatible with the active compound, use thereof in the compositions is contemplated. Supplementary active compounds can also be incorporated into the compositions. Pharmaceutical compositions are described in more detail below.

In another embodiment, compounds that modulate a biological response regulated by, for example, an osteoblast/osteoclast regulator are identified by contacting transgenic cells ex vivo with one or more test compounds, and determining the effect of the test compound on a read-out. In one embodiment, transgenic cells contacted with a test compound ex vivo can be readministered to a subject.

For practicing the screening method ex vivo, transgenic cells can be isolated from a non-human transgenic animal or embryo by standard methods and incubated (i.e., cultured) in vitro with a test compound. Cells (e.g., T cells, B cells, osteoblasts, osteoclasts, and/or stem cells) can be isolated from transgenic animals by standard techniques. In another embodiment, the cells are isolated form animals deficient in one or more of an osteoblast/osteoclast regulator, NFATc1, and/or WWP1, and overexpressing WWP1.

Following contact of the transgenic cells with a test compound (either ex vivo or in vivo), the effect of the test compound on the biological response regulated by an osteoblast/osteoclast regulator can be determined by any one of a variety of suitable methods, such as those set forth herein, e.g., including light microscopic analysis of the cells, histochemical analysis of the cells, production of proteins, induction of certain genes, degradation of certain proteins, e.g., ubiquitination of certain proteins, as described herein.

It will be understood by those of skill in the art that the subject assays may be used in combination to provide various levels of testing for compounds. For example, in one embodiment, a cellular indicator composition comprising an osteoblast/osteoclast regulator, or biological active fragment thereof is contacted with each member of a library of test compounds. An indicator of the activity of the osteoblast/osteoclast regulator is measured. A compound(s) of interest that modulates the activity of the osteoblast/osteoclast regulator polypeptide is selected. The compound of interest may then be tested in a secondary screening assay. For example, the ability of the test compound of interest to increase mesenchymal stem cell differentiation may be tested.

In another embodiment, a compound of interest may be assayed in an in vivo model for its ability to modulate bone formation and mineralization in a non-human adult animal. For example, the test compound may be administered to the animal and the effect of test compound on bone formation and mineralization in the presence and absence of the test compound determined, wherein an increase in bone formation and mineralization in the non-human animal identifies the test compound of interest as a compound that increases bone formation and mineralization. It will be understood that this assay may be used as a secondary screen, a tertiary screen, or a quaternary screen.

D. Test Compounds

A variety of test compounds can be evaluated using the screening assays described herein. The term "test compound" includes any reagent or test agent which is employed in the assays of the invention and assayed for its ability to influence the expression and/or activity of an osteoblast/osteoclast regulator. More than one compound, e.g., a plurality of compounds, can be tested at the same time for their ability to modulate the expression and/or activity of, e.g., an osteoblast/osteoclast regulator in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening can be used to assay for the activity of a compound.

In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909) peptoids (Zuckermann. (1994). *J, Med. Chem.* 37:2678) oligocarbamates (Cho et al. (1993). *Science.* 261: 1303-), and hydantoins (DeWitt et al. supra). An approach for the synthesis of molecular libraries of small organic molecules with a diversity of 104-105 as been described (Carell et al. (1994). Angew. Chem. Int. Ed. Engl. 33:2059-; Carell et al. (1994) Angew. *Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12: 145). Other exemplary methods for the synthesis of molecular libraries can be found in the art, for example in: Erb et al. (1994). *Proc. Natl. Acad. Sci. USA* 91:11422-; Horwell et al. (1996) *Immunopharmacology* 33:68-; and in Gallop et al. (1994); *J. Med. Chem.* 37:1233-.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthetases, isomerases, polymerases, kinases, phosphatases, oxido-reductases and ATPases), and 6) mutant forms of an osteoblast/osteoclast regulator (e.g., dominant negative mutant forms of the molecule).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g. Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

Computer-based analysis of a protein with a known structure can also be used to identify molecules which will bind to a molecule of the invention. Such methods rank molecules based on their shape complementary to a receptor site. For example, using a 3-D database, a program such as DOCK can be used to identify molecules which will bind to, e.g., TAOK2. See DesJarlias et al. (1988) J. Med. Chem. 31:722; Meng et al. (1992) J. Computer Chem. 13:505; Meng et al. (1993) Proteins 17:266; Shoichet et al. (1993) Science 259: 1445. In addition, the electronic complementarity of a molecule to a targeted protein can also be analyzed to identify molecules which bind to the target. This can be determined using, for example, a molecular mechanics force field as described in Meng et al. (1992) J. Computer Chem. 13:505 and Meng et al. (1993) Proteins 17:266. Other programs which can be used include CLIX which uses a GRID force field in docking of putative ligands. See Lawrence et al. (1992) Proteins 12:31; Goodford et al. (1985) J. Med. Chem. 28:849; Boobbyer et al. (1989) J. Med. Chem. 32:1083.

Compounds identified in the subject screening assays can be used in methods of modulating one or more of the biological responses regulated by an osteoblast/osteoclast regulator. It will be understood that it may be desirable to formulate such compound(s) as pharmaceutical compositions (described supra) prior to contacting them with cells.

Once a test compound is identified that directly or indirectly modulates, e.g., an osteoblast/osteoclast regulator expression or activity one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

The instant invention also pertains to compounds identified in the subject screening assays.

VI. Methods of Treatment/Pharmaceutical Compositions

In one embodiment, the subject assays may be used to identify compounds useful in prophylactic treatment of subjects that would benefit from enhanced bone formation. In another embodiment, the subject assays may be used to identify compounds useful in the therapeutic treatment of subjects that would benefit from enhanced bone formation, mineralization and/or osteoclastogenesis, e.g., by modulating an osteoblast/osteoclast regulator biological activity. In one embodiment, a subject that would benefit from enhanced bone formation is an adult subject, e.g., a female subject. In one embodiment, a compound identified using the instant methods may be used to enhance bone healing, e.g., alone or in combination with other therapeutic modalities.

Agents for use in the therapeutic methods of the invention may be known (e.g., dominant negative inhibitors of TAOK2, DLG1, PIN1, LYK5, MOBKL2C, MAP4K2, PACSIN2, DCAMKL1, DOCK4, PARG1, TAOK3, TRPV6, CLK1, AAK1, PRKCA, AKAP8, DGKI, SMARCB1, CIB2, STK33, STK39, NRGN, PIK3R1, RASSF5, FRAP1, STK38, LATS1, LATS2, STK38L, GEFT, TNNI3K, STK4, RAF1, ARF1, C17orf31, EXO1, POT1, TERF2IP, MSH2, DKC1, MOBKL1A, MAP3K11, WWP2, SMURF2, GCK, WASF1, PPP2CB, PPP2R1A, CREBBP, CUL3, FBXW11, MELK, PLCL1, MAP3K3, DLGH1, NEK7, IRAK3, RHOC, SLC4A2, PLCB4, B-RAF, BMPR2, MAPK3, and NHEDC2 activity, osteoblast/osteoclast regulator antisense molecules, intracellular antibodies that interfere with osteoblast/osteoclast regulator activity, peptide inhibitors derived from osteoblast/osteoclast regulator) or can be identified using the methods described herein.

Exemplary disorders that would benefit from increased bone formation by, for example, increasing the expression and/or activity of a positive osteoblast regulator, and/or negative osteoclast regulator, include: erosive arthritis, bone malignancies, osteoporosis, including idiopathic osteoporosis, secondary osteoporosis, transient osteoporosis of the hip, osteomalacia, skeletal changes of hyperparathyroidism, chronic renal failure (renal osteodystrophy), osteitis deformans (Paget's disease of bone), osteolytic metastases, and osteopenia in which there is progressive loss of bone density and thinning of bone tissue are conditions which would benefit from increased bone formation and mineralization such that breaks and/or fractures would not occur. Osteoporosis and osteopenia can result not only from aging and reproductive status, but can also be secondary to numerous diseases and disorders, as well as due to prolonged use of numerous medications, e.g., anticonvulsants (e.g., for epilepsy), corticosteroids (e.g., for rheumatoid arthritis and asthma), and/or immunosuppressive agents (e.g., for cancer). For example, glucocorticoid-induced osteoporosis is a form of osteoporosis that is caused by taking glucocorticoid medications such as prednisone (Deltasone, Orasone, etc.), prednisolone (Prelone), dexamethasone (Decadron, Hexadrol), and cortisone (Cortone Acetate). These medications are frequently used to help control many rheumatic diseases, including rheumatoid arthritis, systemic lupus erythematosus, inflammatory bowel disease, and polymyalgia rheumatica. Other diseases in which osteoporosis may be secondary include, but are not limited to, juvenile rheumatoid arthritis, diabetes, osteogenesis imperfecta, hyperthyroidism, hyperparathyroidism, Cushing's syndrome, malabsorption syndromes, anorexia nervosa and/or kidney disease. In addition, numerous behaviors have been associated with osteoporosis, such as, prolonged inactivity or immobility, inadequate nutrition (especially calcium, vitamin D), excessive exercise leading to amenorrhea (absence of periods), smoking, and/or alcohol abuse. Furthermore, promoting the induction of bone formation and mineralization may be beneficial to treat, for example a bone fracture or break, a tooth replacement, either replacement of a subjects' own tooth or a prosthetic tooth, or ameliorate symptoms of an ongoing condition, such as for example, bone loss associated with, for example peri-menopause or menopause.

In addition, compounds of the invention which modulate an osteoblast/osteoclast regulator activity as a means of downmodulating bone formation, mineralization, and/or osteoclastogenesis is also useful in therapy. For example, decreasing or inhibiting bone formation and mineralization by, e.g., increasing the expression and/or activity of a negative osteoblast regulator, and/or positive osteoclast regulator is beneficial in diseases, disorders, conditions or injuries in which there is premature fusing of two or more bone, or bone density is too high, such as for example, craniosynostosis (synostosis), osteopetrosis (including malignant infantile form, intermediate form, and adult form), primary extra-skeletal bone formation, e.g., multiple military osteoma cutis of the face, and osteitis condensans.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition will preferably be sterile and should be fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as mannitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the test compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

VII. Kits of The Invention

Another aspect of the invention pertains to kits for carrying out the screening assays, modulatory methods or diagnostic assays of the invention. For example, a kit for carrying out a screening assay of the invention can include an indicator composition comprising an osteoblast/osteoclast regulator, means for measuring a readout (e.g., protein secretion) and instructions for using the kit to identify modulators of biological effects of an osteoblast/osteoclast regulator. In another embodiment, a kit for carrying out a screening assay of the invention can include cells deficient in an osteoblast/osteoclast regulator, means for measuring the readout and instructions for using the kit to identify modulators of a biological effect of an osteoblast/osteoclast regulator.

In another embodiment, the invention provides a kit for carrying out a modulatory method of the invention. The kit can include, for example, a modulatory agent of the invention (e.g., an osteoblast/osteoclast regulator inhibitory or stimulatory agent) in a suitable carrier and packaged in a suitable container with instructions for use of the modulator to modulate a biological effect of an osteoblast/osteoclast regulator.

Another aspect of the invention pertains to a kit for diagnosing a disorder associated with a biological activity of an osteoblast/osteoclast regulator in a subject. The kit can include a reagent for determining expression of an osteoblast/osteoclast regulator (e.g., a nucleic acid probe for detecting an osteoblast/osteoclast regulator mRNA or an antibody for detection of an osteoblast/osteoclast regulator protein), a control to which the results of the subject are compared, and instructions for using the kit for diagnostic purposes.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

This invention is further illustrated by the following examples which should not be construed as limiting. The contents of all references, patents, and published patent applications cited throughout this application, as well as the figures and the sequence listing, are hereby incorporated by reference.

EXAMPLES

The following materials and methods were used throughout the Examples:
Bone and Cartilage Staining Newborn mice were skinned, eviscerated and dehydrated in 95% ETOH overnight. The samples wee then transferred into acetone for an additional forty-eight hour incubation. Skeletal preparations were stained for four days using alcian blue and alizarin red as described previously (McLeod, M. J. (1980). *Teratology* 22, 299-301). Following staining, the samples were washed for thirty minutes, three times in 95% ETOH. The soft tissue was then cleared in 1% KOH.
Histomorphometric Analysis For analysis of in vivo bone formation, calcein (1.6 mg/kg body weight) was administered by intraperitoneal injection to 2 month old WT and Shn3$^{-/-}$ mice at 8 days and 3 days prior to sacrifice. Tibias were harvested, cleared of soft tissue and fixed in 70% ethanol. Histomorphometric analysis was conducted by Development and Discovery Services at Charles River Laboratories. Briefly, bones were embedded in methylmethacrylate blocks without decalcification. Sections were stained with Von Kossa and Toluidine Blue or left unstained. Histomorphometry was performed in the secondary spongiosa approximately 1 mm below the lowest portion of the growth plate. Analysis was conducted with Bioquant True Colors software utilizing an Olympus BX-60 fluorescence-equipped microscope and an Optronics digital camera system.
Cell and Tissue Cultures For in vitro osteoclastogenesis, bone marrow cells were isolated from the femur and tibia of mice in αMEM (Mediatech, Inc.). After red blood cell lysis, the cells were washed once and resuspended in αMEM+10% FBS. The bone marrow cells were then plated in a 48-well plate at a concentration of 2×10$^5$ cells per 250 µl of αMEM+10% FBS. The cells were then cultured for two days in the presence of 50 ng/ml M-CSF (Peprotech). After the initial two day culture period, the cells were then cultured for an additional five days in the presence of M-CSF (50 ng/ml) and either 25 ng/ml or 100 ng/ml RANKL (Peprotech). The cells were then fixed and stained for the presence of tartate-resistant alkaline phosphatase (TRAP) per manufacture's instructions (Sigma).

Osteoblastic cells were isolated from calvariae of neonatal WT and Shn3$^{-/-}$ littermates as previously described (Yoshida, Y., et al. (2000). *Cell* 103, 1085-1097). Calvarial-derived cells were plated in αMEM+10% FBS+50 µg/ml ascorbic acid+5 mM β-glycerophosphate in a 6-well dish. Cells were harvested at a sub-confluent stage and replated in a 6-well dish at a concentration of 10$^4$ cells/cm2 in αMEM+10% FBS+50 µg/ml ascorbic acid+5 mM β-glycerophosphate. For von Kossa staining, cells were fixed at day 21 of culture with 10% neutral buffered formalin and stained with 5% silver nitrate for 30 minutes. For ALP, cultures were fixed in 100% ethanol at day 14 of culture, and stained utilizing an alkaline phosphatase kit (Sigma) per manufacturer's instructions. For cell proliferation assays, calvarial-derived cells (10$^5$ cells/well at day 0) were plated in 6-well dish in αMEM+10% FBS+50 µg/ml ascorbic acid+5 mM β-glycerophosphate. Cells were harvested and counted at day 5 of culture utilizing a hemocytometer following trypan blue exclusion staining for cell viability.
Bone Marrow Transfers Bone marrow cells were collected from the femur and tibia of 8-week old WT mice by flushing with RPMI 1640 (Mediatech, Inc.)+10% FBS using a syringe with a 26-gauge needle. Following RBC lysis, cells were washed in RPMI 1640+10% FBS and resuspended in PBS (Gibco). 1×10$^7$ WT bone marrow cells were then transferred by tail vein injection into γ-irradiated (1200 rads) 4-week old WT and Shn3$^{-/-}$ mice. The irradiated mice were analyzed by radiography four weeks after transfer.
Quantitative Real-Time PCR For quantitative real-time PCR, total RNA was extracted from Shn3$^{-/-}$ and WT osteoblasts and at day 14 of culture utilizing Trizol (Invitrogen). Reverse transcription was performed on 11 g RNA using iScript cDNA Synthesis kit (Bio-Rad) following the treatment of isolated RNA with amplification-grade DNase I (Invitrogen). Quantitative PCR was then performed on an ABI Prism 7700 Sequence Detection System (Applied Biosystems). PCR reaction were carried out in 25 µl volumes using SYBR Green PCR master mix (Applied Biosystems) and 0.2 µM of specific primers. Relative levels of mRNA for a specific gene between two samples were calculated utilizing the ΔΔCT method where the amount of cDNA in each sample was normalized to the β-actin Ct (Livak, K. J., and Schmittgen, T. D. (2001). *Methods* 25, 402-408).
Transient Transfections and Reporter Gene Assays The preosteoblast cell line, MC3T3-E1 Subclone 4, and the murine mesenchymal stem cell line, C3H10T1/2, were obtained from ATCC and maintained in DMEM (Mediatech, Inc.)+10% FBS. For transient transfections, cells were seeded overnight in a 12-well dish at a concentration of 8×10$^4$ cells/well. Cells were then transfected with a luciferase reporter gene plasmid and the different combinations of expression constructs, as indicated, using Effectene transfection reagent (Qiagen). Total amounts of transfected DNA were kept constant by supplementing with control empty expression vector plasmids as needed. All cells were cotransfected with pRL-TK (Promega) as a normalization control for transfection efficiency. Forty-eight hours after transfection, cells were harvested and lysed in 1× Passive Lysis Buffer (Promega). Luciferase assays were performed using the Dual-Luciferase Reporter Assay System (Promega). The Shn3 expression plasmid has been described previously (Oukka, M., et al. (2002). *Mol Cell* 9, 121-131).

Immunoprecipitation and Immunoblotting

For immunoprecipitation, 293T cells ($6 \times 10^6$ cells/dish) were plated in 10 cm dishes in DMEM+10% FBS and transiently transfected with Effectene transfection reagent. Thirty-six to forty-eight hours later, cells were harvested and lysed in TNT lysis buffer (20 mM Tris, pH 8.0, 200 mM NaCl, 0.5% Triton X-100) supplemented with protease inhibitors. Lysates were subjected to immunoprecipitation with agarose-conjugated anti-FLAG (M2, Sigma) or anti-Myc (9E10, Santa Cruz) monoclonal antibodies at 4° C. overnight. Immunoprecipitates were then washed three times in lysis buffer and subjected to SDS-PAGE followed by immunoblotting for Shn-3 (Oukka, M., et al. (2002). *Mol Cell* 9, 121-131), FLAG (M2, Sigma), or Myc (9E10, Santa Cruz).

To detect the interaction between endogenous Shn3 and Runx2, MC3T3-E1 cells were grown to confluency in DMEM+10% fetal calf serum in 10 cm dishes. When cells reached confluency, medium was changed to αMEM+10% fetal calf serum supplemented with 10 mM β-glycerophosphate, 50 μM ascorbic acid, and with or without BMP-2 (100 ng/ml), as described (Zamurovic, N., et al. (2004). *J Biol Chem* 279, 37704-37715). Cells were differentiated for an additional 3-4 days. Eighteen-hours prior to lysis TGFβ (2 ng/ml, R+D Systems) was added to some cultures, and 2 hours prior to lysis MG132 (10 μM, Boston Biochem) was added to all cultures. Cells were harvested and lysed in TNT buffer. Lysates were subjected to immunoprecipitation with 3 μg anti-Runx2 antibody (Santa Cruz) or control rabbit IgG at 4° C. overnight. Protein A/G-agarose (Santa Cruz) was added to precipitate immune complexes, which were then washed five times with lysis buffer followed by SDS-PAGE and immunoblotting for Shn3.

Additional co-immunoprecipitation experiments were conducted with FLAG-epitope-tagged Runx2 deletion mutants. Full length (amino acids 1-521) contains QA, Runt and PST domains. QA mutant (amino acids 48-89) contains QA domain but lacks both Runt and PST domains. Runt mutant (amino acids 102-229) contains Runt and PST domain. Runt/PST mutant (amino acids 102-521) contains Runt and PST domain but lacks QA domain. Shn3 interaction with these mutants was determined by Western blot analysis with anti-Shn3 antibody following immunoprecipitation with anti-FLAG antibody.

To detect endogenous Atf4 and Runx2 protein levels in Shn3$^{-/-}$ and WT osteoblasts, calvarial osteoblast cultures at days 14 and 21 were lysed in RIPA buffer supplemented with protease inhibitors. Protein concentrations were determined and 50 μg protein per sample was resolved by SDS-PAGE followed by immunoblotting for Runx2 (EMD Biosciences), Atf4 (Santa Cruz), or Hsp90 (Santa Cruz).

Ubiquitination Assays

To detect ubiquitination of Runx2 in 293T cells, a previously established protocol was followed (Campanero, M. R., and Flemington, E. K. (1997). *Proc Natl Acad Sci USA* 94, 2221-2226). In brief, 293T cells were transiently transfected with combinations of His-Ub, FLAG-Runx2, Myc-WWP1, and Shn3. Thirty-six to forty-eight hours later, cells were treated with 10 μM MG132 for 2 hours. Cells were washed and lysed in buffer containing 6M guanidium-HCl. Ubiquitinated proteins were precipitated with Ni-NTA-agarose (Novagen), and washed in lysis buffer followed by wash buffer containing 25 mM Tris pH 6.8, 20 mM imidazole. Precipitates were resolved by SDS-PAGE and ubiquitinated FLAG-Runx2 was detected by immunoblotting with anti-FLAG (M2, Sigma) antibody.

To assay the ability of immunoprecipitated Runx2/Shn3 complexes to promote ubiquitination in vitro, various combinations of FLAG-Runx2 and Shn3 were transiently transfected in 293T cells as above. Thirty-six to forty-eight hours later, cells were treated with 10 μM MG132 for 2 hours. Cells were washed, lysed in TNT buffer, and anti-FLAG immunoprecipitations were performed as above. Immune complexes were washed in TNT buffer, then in ubiquitination assay (UA) buffer containing 50 mM Tris, pH 8, 50 mM NaCl, 1 mM DTT, 5 mM MgCl2, and 1 mM ATP. Immunoprecipitates were resuspended in UA buffer supplemented ubiquitin and biotinylated ubiquitin (Boston Biochem) with or without recombinant E1, and E2 (UbCH5a and UbCH7, Boston Biochem). Ubiquitination reactions were allowed to proceed at 30° C. for two hours. Reactions were subsequently resolved by SDS-PAGE, transferred to PVDF membranes, and ubiquitinated proteins were visualized by blotting with streptavidin-HRP (Zymed).

Pulse-Chase Analysis 293T cells ($1 \times 10^6$ cells) were transiently transfected with FLAG-Runx2 (200 ng) with or without Shn3 (1 μg) in 6 well plates. After thirty-six hours, cells were washed and incubated in cysteine/methionine-free medium for one hour. Cells were then labeled with 0.1 mCi/ml S$^{35}$-labelled cysteine/methionine for one hour. Next, cells were chased in medium containing excess non-radioactive cysteine/methionine for the indicated times. Cells were collected and lysed in TNT buffer supplemented with protease inhibitors, and anti-FLAG immunoprecipitations (M2 agarose slurry, Sigma) were performed at 4° C. overnight. Immunoprecipitates were washed four times in lysis buffer, resolved by SDS-PAGE, and immunoprecipitated proteins were visualized by fluography and quantified with PhosphoImager.

Transient Runx2 Reporter Assay

C3H10T1/2 cells are passaged in DMEM supplemented with 10% fetal calf serum. Cells are seeded in 12 well dishes at $6 \times 10^4$ cells per well. The next day, cells are transfected with 6×OSE2-firefly luciferase, pTK-renilla luciferase, Runx2 and Shn3 cDNA expression constructs using Effectene transfection reagent (Qiagen). Twenty-four hours later, the medium is changed and compounds dissolved in DMSO, or DMSO-only controls, are added. Eighteen hours later, cells are harvested and analyzed for firefly and renilla luciferase activity according to the manufacturer's instructions (Promega). Compounds that block KRC-mediated repression of Runx2-driven transcriptional activity are scored as positive in this assay.

C3H-Runx2 Cell Assay

C3H10T1/2 cells are infected with control (RV-GFP) or Runx2-expression (RV-Runx2) retroviruses. Retrovirally-infected cells are further purified by cell sorting based on GFP expression. GFP-positive, RV-Runx2 infected cells are determined to express high levels of osteoblast markers Osterix, alkaline phosphatase, osteocalcin, and bone sialoprotein by RT-PCR. Furthermore, Runx2 protein levels in RV-Runx2 cells are increased following WWP1 RNAi. To screen compounds, RV-Runx2 cells are plated in 96 well plates at $6 \times 10^3$ cells per well in DMEM-10% medium. Twenty-four hours later, the medium is changed and replaced with osteogenic medium containing 5 mM beta-glycerophosphate and 50 mg/L ascorbic acid along with test compounds and DMSO-only controls. Seventy-two hours later, alkaline phosphatase activity is determined according to the manufacturer's instructions (Sigma) and normalized to cell number per well determined by Alamar Blue staining. Compounds that increase alkaline phosphatase activity are scored as positive in this assay.

Standard WWP1 Ubiquitin Ligase Assay

Ubiquitin ligase assays are performed in 20 µl reaction volumes containing 20 mM Tris-Hcl pH 8, 50 mM NaCl, 5 mM MgCl2, 1 mM ATP, 1 mM DTT, 50 ng E1 (yeast, Boston Biochem), 50 ng E2 (UbCH7, Boston Biochem) and 100 ng recombinant HECT domain of WWP1. Reactions include 100 ng biotinylated ubiquitin (Boston Biochem) to facilitate detection of assay products. Reactions are assembled on ice, and test compounds or DMSO controls are added. Assays are conducted for 15 minutes at 30 degrees C., and immediately stopped with SDS-sample buffer. Reactions are separated by SDS-PAGE and products detected by blotting with streptavidin-HRP (Zymed). Compounds that block WWP1 ubiquitin ligase activity are scored as positive in this assay.

High Throughput WWP1 Ubiquitin Ligase Assay

Myc-tagged WWP1 is overexpressed in 293T cells using Effectene (Qiagen). 48 hours later, whole cell lysates are prepared in lysis buffer (20 mM Tris pH 8, 250 mM NaCl, 3 mM EDTA, 0.5% Triton X-100) and lysates are aliquoted and frozen at −80 degrees C. until future use. Ninety-six well plates are coated with anti-Myc monoclonal antibody (9E10, Santa Cruz) at 4 degrees C. overnight. The next morning, plates are washed and blocked in 3% BSA dissolved in PBS for 2-3 hours at room temperature. Plates are then washed and 293T cell lysate is incubated with antibody-coated plates overnight at 4 degrees C. The next morning, plates are washed and incubated with ubiquitin ligase assay mixture (as above) containing biotinylated ubiquitin on ice. Compounds are added and the reaction is allowed to continue at 30 degrees C. for 30 minutes. Plates are washed and incubated with streptavidin-coupled alkaline phosphatase followed by standard alkaline phosphatase colorimetry. Compounds that block WWP1 autoubiquitination activity are scored as positive in this assay.

Human Mesenchymal Stem Cell (hMSC) Culture

For in vitro osteoblast differentiation, hMSCs (Cambrex) were maintained and differentiated following manufactures protocols. hMSCs were plated in Optilux 96-well plates (BD Biosciences) at a concentration of $3.1 \times 10^3$ cell per cm$^2$ in MSC growth media (MSGM). Following an overnight incubation, the growth media was replaced with osteogenic induction media (Cambrex) that contained compounds or vehicle. Cells were cultured in the presence of the compounds or vehicle for seven days at which point osteoblast differentiation was assayed by alkaline phosphatase expression.

To assess extracellular matrix formation, hMSCs were cultured under osteogenic conditions as described above in the presence of the compounds or vehicle for twenty-one days. The growth media was changed every three days for the duration of the culture period. At each media change, the compounds or vehicle were added fresh to the cell cultures. Xyelonol orange (Sigma) was then added to the growth media for an eighteen-hour period at day twenty-one of culture. Each of the cultures was then examined by fluorescent microscope to visualize the formation of extracellular matrix.

Alkaline Phosphatase Index (API)

To determine API, cell numbers were first established by culturing cells in media containing Alamar blue (Biosource) for 4 hours at 37° C. Plates were read on a fluorimeter at 570 nm. Media containing Alamar Blue was removed and cells were washed 1× with sterile PBS. Cells were then incubated with alkaline phosphatase substrate (Sigma) for 1 hour at room temperature. Following incubation period, the plate was read at 405 nm. Alkaline phosphatase levels were then normalized to cell number to establish API (API=Alk. Phos./alamar blue).

Example 1

An RNAi Screening Approach to Identify Novel Regulators of Osteoclast Differentiation Osteoclast differentiation is a complex process requiring the integration of signaling and transcriptional networks. Positive and negative regulators of this process remain to be identified. Post-transcriptional mRNA silencing though RNAi technology permits the assessment of gene function in vitro and in vivo without the cost and time associated with the generation of genetically deficient animals or cell lines (Hannon, G. J., and J. J. Rossi. 2004. *Nature* 431:371-378). Implementation of RNAi into arrayed libraries provides a screening tool to identify novel molecules involved in cellular processes. To date, this technology has not been used to probe osteoclast development. A lentiviral shRNA library directed against murine kinases, phosphatases, phospholipases, receptors, and transcription factors developed at the Broad Institute has been used. This library targets each gene with 5 different shRNA constructs and has recently been used to identify regulators of mitosis (Moffat, J., et al. 2006. *Cell* 124:1283-1298). Primary, secondary and tertiary screens have been performed and known, as well as potentially novel, genes involved in osteoclast differentiation have been identified.

Assay Development.

Osteoclast differentiation can be reproduced in vitro using a mouse macrophage cell line, RAW 264.7, and recombinant RANKL (Ishida, N., et al. 2002. *J Biol Chem* 277:41147-41156.). Mature osteoclasts, but not their precursors, secrete the enzyme TRAP, which can be assayed in the culture supernatant with a colorimetric assay. Moreover, TRAP secretion is associated with the activated osteoclast phenotype (Kirstein, B., et al. 2006. *J Cell Biochem*). A stepwise approach to assay development was taken.

RAW 264.7 cells (osteoclast precursors) are transduced with individual lentiviral clones in 96 well plates. Each clone encodes an shRNA with a different mRNA specificity, as well as a puromycin resistance gene. Each mRNA is targeted with 5 different lentiviral clones. Stable transductants are selected using puromycin. RANKL is added to the culture media for 4 days to stimulate osteoclast differentiation, which is quantified by measuring the amount of TRAP released into the culture supernatant. To control for wells with low, or absent, viral titers, the total cellular mass per well is quantified using the Alamar blue assay (Invitrogen). This sensitive fluorescence based assay measures the metabolic activity of live cells and is quantitative over 4 logs of cell density. The Alamar blue result is then plotted against the TRAP activity to generate an XY scatter plot. A best-fit line is generated and used to derive a predicted TRAP activity for a given Alamar blue reading. Subsequently, an osteoclast index (OCI), defined as the observed TRAP activity divided by the predicted TRAP activity multiplied by 100, is calculated for each sample.

Results of the Primary and Secondary Screen 3,271 lentiviral shRNA clones corresponding to 651 genes were screened. Using a cutoff of at least 2 lentiviral shRNAs per gene yielding an OCI one standard deviation above or below the mean OCI of the entire population, 161 potential genes involved in osteoclastogenesis were identified. In a secondary screen, each of the 5-lentiviral shRNA constructs against the 161 potential regulators identified in the primary screen was repeated in duplicate. The OCIs were compared to the average OCI generated from a plate consisting of 90 negative control shRNA constructs designed to recognize sequences in non-eukaryotic genes. From the secondary screen, 42 potential positive regulators (the lentiviral shRNA constructs decreased TRAP activity) and 4 potential negative regulators (the lentiviral shRNA constructs increased TRAP activity) were identified. Included within the 42 potential positive regulators were 6 genes known to be important for osteoclastogenesis. These include the kinases, IKKβ, mTOR, PI3-kinase, NIK and Syk, as well as the transcription factor, PU.1 (Wada, T., et al. 2006. Trends Mol Med 12:17-25; Kuhn, R., et al. 1995. Science 269:1427-1429; Sugatani, T., and K. A. Hruska. 2005. J Biol Chem 280:3583-3589). Mice deficient in IKKβ, Syk and PU.1 are osteopetrotic and deficient in osteoclasts. Furthermore, PU.1 directly promotes TRAP gene expression, the readout in the assay (Cassady, A. I., et al. 2003. J Bone Miner Res 18:1901-1904).

From a tertiary screen using newly prepared shRNA vectors, 19 potential positive regulators and 2 potential negative regulators were identified. Included, were 5 of the 6 genes known to mediate osteoclastogenesis.

Correlating Knockdown with Phenotype

A systematic approach, using RT-PCR, has been developed to correlate the degree of target knockdown by lentiviral shRNA clones that altered osteoclast differentiation in this screen.

RAW 264.7 cells are infected with 5 different LV-shRNA constructs Stable transductants will be selected with puromycin and differentiated for 4 days with RANKL. mRNA will be purified and analyzed by qRT-PCR for shRNA target gene expression, and for genes associated with osteoclast differentiation, including NFATc1, TRAP, Cathepsin K, MMP9, β3-integrin and Calcitonin receptor (as in FIG. 11). Cells infected with control viruses directed against different sequences in GFP will serve as controls. Parallel cultures will be stained for TRAP and the number of TRAP positive, multinucleated giant cells enumerated microscopically. Knockdown of target gene expression will be correlated with the formation of multinucleated giant cells and osteoclast specific gene expression. The Alamar blue assay will be used to assess cell number and control for toxicity in these experiments.

All 5 lentiviral shRNA clones directed against Pu.1 yielded significant decreases in osteoclast differentiation. Accordingly, all 5 clones reduced Pu.1 mRNA levels by 80% or more compared to cells infected with control viruses. For Syk, clones 1, 4 and 5 yielded a significant reduction in osteoclast differentiation in this experiment. These clones all reduced Syk mRNA levels. As important, Syk clones 2 and 3 neither affected osteoclast differentiation nor significantly reduced target gene expression.

As a second method to validate potential osteoclast regulators identified in the shRNA screen, additional lentiviral shRNA constructs will be made and tested in osteoclast assays in vitro using RAW cells and BMOcPs. By generating new shRNA vectors with different target sequences, the "hits" can be independently validated by RNAi technology. Fortunately, the Broad institute RNAi platform, which produced the lentiviral shRNA library used for our screen, has generated an "in silico" list of shRNA vectors for every gene in the mouse and human genome. This list includes more than 50 potential constructs per gene and is ranked based upon a prediction model that selects for specificity and knockdown efficiency.

Oligonucleotides corresponding to the shRNA sequence are ordered and cloned into lentiviral expression vectors provided by the Broad Institute with a puromycin selection marker. Lentiviral supernatants will be prepared and used to infect either RAW 264.7 cells or WT BMOcPs. RNA will be prepared from stably transduced cells and knockdown efficiency will be assessed by RT-PCR. Those viruses that yield greater than 80% knockdown of the target transcript will be used to infect RAW 264.7 cells or WT BMOcPs. Stable transductants will be incubated with RANKL for 4 days. A scrambled shRNA sequence will be used as a negative control. The number of TRAP positive multinucleated giant cells (Osteoclasts) will be enumerated microscopically. mRNA will be purified and analyzed by RT-PCR for NFATc1, TRAP, Cathepsin K, MMP9, β3-integrin and the Calcitonin receptor. Lastly, the infection and differentiation protocol will be carried out on cells plated on Bio-Coat osteologic slides (Becton-Dickenson) and matrix resorption quantified by Silver nitrate staining and transmitted light microscopy. The Alamar blue assay will be used to assess cell number and control for toxicity in these experiments

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying a compound useful in inhibiting osteoclast differentiation comprising,
   a) providing an indicator composition comprising a hematopoietic stem cell comprising an osteoclast regulator SLC4A2;
   b) contacting the indicator composition with each member of a library of test compounds under conditions that promote osteoclast differentiation, wherein such conditions comprise culture in the presence of Receptor Activator of Nuclear factor Kappa B Ligand (RANKL);
   c) evaluating (i) expression and/or activity of SLC4A2 in the indicator composition in the presence and absence of the test compound, and (ii) osteoclast differentiation in the indicator composition in the presence and absence of the test compound; and
   d) selecting a test compound that (i) inhibits SLC4A2 expression and/or activity in the presence of the test compound, as compared to SLC4A2 expression and/or activity in the absence of the test compound, and (ii) inhibits osteoclast differentiation in the presence of the test compound, as compared to osteoclast differentiation in the absence of the test compound, to thereby identify a compound useful in inhibiting osteoclast differentiation.

2. A method of identifying a compound useful in stimulating osteoclast differentiation comprising,
   a) providing an indicator composition comprising a hematopoietic stem cell comprising an osteoclast regulator SLC4A2;
   b) contacting the indicator composition with each member of a library of test compounds under conditions that promote osteoclast differentiation, wherein such conditions comprise culture in the presence of Receptor Activator of Nuclear factor Kappa B Ligand (RANKL);
   c) evaluating (i) expression and/or activity of SLC4A2 in the indicator composition in the presence and absence of the test compound, and (ii) osteoclast differentiation in the indicator composition in the presence and absence of the test compound; and
   d) selecting a test compound that (i) stimulates SLC4A2 expression and/or activity in the presence of the test compound, as compared to SLC4A2 expression and/or activity in the absence of the test compound, and (ii) stimulates osteoclast differentiation in the presence of the test compound, as compared to osteoclast differentiation in the absence of the test compound, to thereby identify a compound useful in stimulating osteoclast differentiation.

3. The method of claim 1, wherein the hematopoietic stem cell is selected from the group consisting of $CD11b^{low/-}$ $CD3^-$ $B220^-$ c-fms$^+$ cells, $CD11b^{low/-}$ $CD3^-$ $B220^-$ c-fms$^+$ c-kit$^+$ cells and $CD11b^{low/-}$ $CD3^-$ $B220^-$ c-fms$^+$ c-kit$^-$ cells.

4. The method of claim 1, wherein the hematopoietic stem cell is a RAW 264.7 cell line.

5. The method of claim 1, wherein osteoclast differentiation is evaluated by assaying secretion of tartrate-resistant acidic phosphatase (TRAP) enzyme.

6. The method of claim 2, wherein the hematopoietic stem cell is selected from the group consisting of $CD11b^{low/-}$ $CD3^-$ $B220^-$ c-fms$^+$ cells, $CD11b^{low/-}$ $CD3^-$ $B220^-$ c-fms$^+$ c-kit$^+$ cells and $CD11b^{low/-}$ $CD3^-$ $B220^-$ c-fms$^+$ c-kit$^-$ cells.

7. The method of claim 2, wherein the hematopoietic stem cell is a RAW 264.7 cell line.

8. The method of claim 2, wherein osteoclast differentiation is evaluated by assaying secretion of tartrate-resistant acidic phosphatase (TRAP) enzyme.

* * * * *